(12) United States Patent
Malinskiy et al.

(10) Patent No.: US 10,932,658 B2
(45) Date of Patent: Mar. 2, 2021

(54) WIRELESS IMAGING SYSTEM COMPRISING A HEAD UNIT AND A LIGHT CABLE THAT COMPRISES AN INTEGRATED LIGHT SOURCE

(71) Applicant: Infinite Arthroscopy, Inc. Limited, Cleveland Heights, OH (US)

(72) Inventors: Eugene Malinskiy, Cleveland Heights, OH (US); Ilya Malinskiy, Cleveland Heights, OH (US); Howard Fein, Cleveland Heights, OH (US); Brad Roskoph, Cleveland Heights, OH (US); Daniel Dudley, Cleveland Heights, OH (US)

(73) Assignee: INFINITE ARTHROSCOPY, INC. LIMITED, Cleveland Heights, OH (US)

( * ) Notice: Subject to any disclaimer, the term of this patent is extended or adjusted under 35 U.S.C. 154(b) by 0 days.

(21) Appl. No.: 16/803,124

(22) Filed: Feb. 27, 2020

(65) Prior Publication Data

US 2020/0187763 A1 Jun. 18, 2020

Related U.S. Application Data

(63) Continuation of application No. 16/321,337, filed as application No. PCT/US2018/018172 on Feb. 14, 2018, now Pat. No. 10,610,089.

(Continued)

(51) Int. Cl.
*H04N 7/18* (2006.01)
*A61B 1/045* (2006.01)
(Continued)

(52) U.S. Cl.
CPC .......... *A61B 1/045* (2013.01); *A61B 1/00029* (2013.01); *A61B 1/0638* (2013.01);
(Continued)

(58) Field of Classification Search
CPC .... H04N 7/185; A61B 1/045; A61B 1/00029; A61B 1/0638; A61B 1/0646; A61B 1/0684; A61B 1/07
(Continued)

(56) References Cited

U.S. PATENT DOCUMENTS

| 5,178,616 A | 1/1993 | Uemiya et al. |
| 5,311,859 A | 5/1994 | Monroe et al. |

(Continued)

FOREIGN PATENT DOCUMENTS

| CN | 101821866 A | 9/2010 |
| CN | 104603530 A | 6/2015 |

(Continued)

OTHER PUBLICATIONS

International Search Report and Written Opinion of the International Searching Authority, dated Apr. 26, 2018, for International Application No. PCT/US2018/018172.

(Continued)

*Primary Examiner* — Shan E Elahi
(74) *Attorney, Agent, or Firm* — Morgan, Lewis & Bockius LLP

(57) ABSTRACT

A wireless imaging system comprising a head unit and a light cable is provided. The head unit comprises a head unit case, a head unit electrical connector, an image sensor, a wireless transceiver, a central processing unit, and a user-input component. The light cable comprises a light cable electrical connector, a power cable, and an integrated light source. The integrated light source comprises an emissive radiation source having a first spectrum, an optical element (Continued)

located to direct emissions from the emissive radiation source, a volumetric spectrum converter, and an optical reflector located about the converter. The converter converts emissions directed from the emissive radiation source to emissions having a second spectrum different from the first spectrum. The reflector reflects the converter emissions towards the output filter.

20 Claims, 18 Drawing Sheets

Related U.S. Application Data

(60) Provisional application No. 62/459,306, filed on Feb. 15, 2017.

(51) Int. Cl.
  *A61B 1/00* (2006.01)
  *A61B 1/06* (2006.01)
  *A61B 1/07* (2006.01)

(52) U.S. Cl.
  CPC .......... *A61B 1/0646* (2013.01); *A61B 1/0684* (2013.01); *A61B 1/07* (2013.01); *H04N 7/185* (2013.01)

(58) Field of Classification Search
  USPC .......................................................... 348/68
  See application file for complete search history.

(56) References Cited

U.S. PATENT DOCUMENTS

| | | | |
|---|---|---|---|
| 5,879,289 A | 3/1999 | Yarush et al. | |
| 6,007,255 A | 12/1999 | Krauter | |
| 6,043,839 A | 3/2000 | Adair et al. | |
| 6,449,006 B1 | 9/2002 | Shipp | |
| 6,494,826 B1 | 12/2002 | Chatenever et al. | |
| 6,806,681 B1 | 10/2004 | Cheiky | |
| 7,091,653 B2 | 8/2006 | Ouderkirk et al. | |
| 7,091,661 B2 | 8/2006 | Ouderkirk | |
| 7,193,248 B2 | 3/2007 | Weindorf et al. | |
| 7,394,188 B2 | 7/2008 | Ouderkirk et al. | |
| 7,442,167 B2 | 10/2008 | Dunki-Jacobs et al. | |
| 7,513,669 B2 | 4/2009 | Chua et al. | |
| 7,553,683 B2 | 6/2009 | Martin et al. | |
| 7,668,450 B2 | 2/2010 | Todd | |
| 7,724,412 B2 | 5/2010 | Powell | |
| 7,777,243 B2 | 8/2010 | Lin et al. | |
| 7,786,879 B2 | 8/2010 | Lax | |
| 7,798,692 B2 | 9/2010 | Krupa | |
| 7,837,348 B2 | 11/2010 | Narendran et al. | |
| 7,839,072 B2 | 11/2010 | Horiuchi et al. | |
| 8,029,439 B2 | 10/2011 | Todd | |
| 8,083,364 B2 | 12/2011 | Allen | |
| 8,088,304 B2 | 1/2012 | Winkler et al. | |
| 8,128,557 B2 | 3/2012 | Scholly et al. | |
| 8,142,051 B2 | 3/2012 | Ducharme | |
| 8,395,312 B2 | 3/2013 | Hum | |
| 8,436,388 B2 | 5/2013 | Lim et al. | |
| 8,519,609 B2 | 8/2013 | Winkler et al. | |
| 8,545,396 B2 | 10/2013 | Cover et al. | |
| 8,558,880 B2 | 10/2013 | Nambakam et al. | |
| 8,562,161 B2 | 10/2013 | Tong et al. | |
| 8,585,273 B2 | 11/2013 | Pokrovskiy et al. | |
| 8,622,893 B2 | 1/2014 | Mathieu | |
| 8,625,097 B2 | 1/2014 | Brukilacchio | |
| 8,632,196 B2 | 1/2014 | Tong et al. | |
| 8,748,921 B2 | 6/2014 | Martin et al. | |
| 8,810,126 B2 | 8/2014 | Ito | |
| 8,827,888 B2 | 9/2014 | Bolyard | |
| 8,841,146 B2 | 9/2014 | Yen et al. | |
| 8,882,284 B2 | 11/2014 | Tong et al. | |
| 8,928,219 B2 | 1/2015 | Chan et al. | |
| 8,946,982 B2 | 2/2015 | Winkler et al. | |
| 9,147,814 B2 | 9/2015 | Waragaya | |
| 9,217,544 B2 | 12/2015 | Tong et al. | |
| 9,217,545 B2 | 12/2015 | Ito | |
| 9,287,469 B2 | 3/2016 | Chakraborty | |
| 9,303,830 B2 | 4/2016 | Ito | |
| 9,316,361 B2 | 4/2016 | Tong et al. | |
| 9,382,472 B2 | 7/2016 | Hefner, Jr. et al. | |
| 9,383,496 B2 | 7/2016 | Parker et al. | |
| 9,404,637 B2 | 8/2016 | Aeling et al. | |
| 9,464,224 B2 | 10/2016 | Deshpande et al. | |
| 9,500,325 B2 | 11/2016 | Tong et al. | |
| 9,551,468 B2 | 1/2017 | Jones | |
| 9,553,230 B2 | 1/2017 | Yoshida et al. | |
| 9,587,791 B2 | 3/2017 | Ito | |
| 9,611,987 B2 | 4/2017 | Kelchner et al. | |
| 9,677,719 B2 | 6/2017 | He et al. | |
| 2002/0120181 A1 | 8/2002 | Irion | |
| 2003/0156430 A1 | 8/2003 | Ota | |
| 2005/0006659 A1 | 1/2005 | Ng et al. | |
| 2005/0093430 A1 | 5/2005 | Ibbetson et al. | |
| 2005/0116635 A1 | 6/2005 | Ito | |
| 2006/0145599 A1 | 7/2006 | Reza et al. | |
| 2006/0171693 A1 | 8/2006 | Todd et al. | |
| 2006/0183976 A1* | 8/2006 | Adler ................. | A61B 1/00193 600/176 |
| 2006/0226759 A1 | 10/2006 | Masuda et al. | |
| 2007/0086205 A1 | 4/2007 | Krupa | |
| 2007/0267967 A1 | 11/2007 | Soshchin | |
| 2008/0048200 A1 | 2/2008 | Mueller et al. | |
| 2008/0183028 A1 | 7/2008 | Garcia et al. | |
| 2008/0261528 A1 | 10/2008 | Rosenblatt | |
| 2009/0034230 A1 | 2/2009 | Lim et al. | |
| 2009/0040523 A1 | 2/2009 | Brukilacchio | |
| 2009/0076328 A1 | 3/2009 | Root et al. | |
| 2009/0151785 A1 | 6/2009 | Soshchin et al. | |
| 2010/0033075 A1 | 2/2010 | Soshchin et al. | |
| 2010/0061077 A1 | 3/2010 | Winkler et al. | |
| 2010/0172148 A1 | 7/2010 | Komazaki et al. | |
| 2010/0298711 A1 | 11/2010 | Pedersen | |
| 2011/0069490 A1 | 3/2011 | Liu | |
| 2011/0157865 A1 | 6/2011 | Takashi | |
| 2011/0172492 A1 | 7/2011 | Erikawa | |
| 2011/0208004 A1 | 8/2011 | Feingold | |
| 2011/0227102 A1 | 9/2011 | Hussell et al. | |
| 2011/0261183 A1 | 10/2011 | Ma et al. | |
| 2012/0029289 A1 | 2/2012 | Kucklick | |
| 2012/0051075 A1 | 3/2012 | Harada et al. | |
| 2012/0071710 A1 | 3/2012 | Gazdzinski | |
| 2012/0116369 A1 | 5/2012 | Viola | |
| 2013/0027962 A1 | 1/2013 | Takashi | |
| 2013/0100264 A1 | 4/2013 | Kazakevich et al. | |
| 2013/0139826 A1 | 6/2013 | Swann et al. | |
| 2013/0140983 A1 | 6/2013 | Ling et al. | |
| 2013/0162767 A1* | 6/2013 | Chou ................. | G02B 23/2415 348/43 |
| 2013/0188383 A1 | 7/2013 | Jaffe | |
| 2013/0314893 A1 | 11/2013 | Paquette | |
| 2013/0324794 A1 | 12/2013 | Cover et al. | |
| 2013/0334546 A1 | 12/2013 | Wagenblast et al. | |
| 2014/0183584 A1 | 7/2014 | Tong et al. | |
| 2014/0221740 A1 | 8/2014 | Kawula et al. | |
| 2014/0275763 A1 | 9/2014 | King | |
| 2014/0320677 A1 | 10/2014 | Jarvenpaa | |
| 2015/0077972 A1 | 3/2015 | Sugiyama et al. | |
| 2015/0115302 A1 | 4/2015 | Eder et al. | |
| 2015/0130935 A1 | 5/2015 | Siann | |
| 2015/0157188 A1 | 6/2015 | Moskowitz et al. | |
| 2015/0182118 A1 | 7/2015 | Bradbury et al. | |
| 2015/0184830 A1 | 7/2015 | Nagao et al. | |
| 2015/0362828 A1 | 12/2015 | Patel et al. | |
| 2015/0366442 A1* | 12/2015 | Amling .............. | A61B 1/00009 348/47 |
| 2016/0004147 A1 | 1/2016 | Hu et al. | |
| 2016/0018100 A1 | 1/2016 | Batt et al. | |
| 2016/0213230 A1 | 7/2016 | Adair et al. | |
| 2016/0248994 A1 | 8/2016 | Liu | |
| 2016/0262597 A1 | 9/2016 | Danchinyu et al. | |

(56) References Cited

U.S. PATENT DOCUMENTS

| | | |
|---|---|---|
| 2017/0003000 A1 | 1/2017 | Narendran et al. |
| 2017/0045201 A1 | 2/2017 | Jones |
| 2018/0245775 A1 | 8/2018 | Malinskiy et al. |

FOREIGN PATENT DOCUMENTS

| | | |
|---|---|---|
| EP | 2822111 A1 | 1/2015 |
| EP | 2941175 A1 | 11/2015 |
| GB | 1542873 A | 3/1979 |
| JP | 2006-518939 A | 8/2006 |
| JP | 2010-0541295 A | 12/2010 |
| JP | 2015060871 A | 3/2015 |
| WO | 2004068903 A2 | 8/2004 |
| WO | 2008087243 A1 | 7/2008 |
| WO | 2009048704 A2 | 4/2009 |
| WO | 2012016224 A2 | 2/2012 |
| WO | 2012025179 A1 | 3/2012 |
| WO | 2013139619 A1 | 9/2013 |
| WO | 2013139620 A1 | 9/2013 |
| WO | 2013139675 A1 | 9/2013 |
| WO | 2015127630 A1 | 9/2015 |
| WO | 2017031138 A1 | 2/2017 |
| WO | 2017087448 | 5/2017 |
| WO | 2018152196 | 8/2018 |

OTHER PUBLICATIONS

Extended European Search Report dated Jan. 29, 2019 for European Patent Application No. 16837714.1, 8 pages.

Notice of Reasons for Rejection dated Feb. 5, 2019 for Japanese Patent Application No. 2018-509824, 10 pages.

First Notification of Office Action dated Dec. 26, 2018 for Chinese Patent Application No. 20168004857.6, 5 pages.

Search Report for Chinese Patent Application No. 201680048579.6, 2 pages.

International Search Report and Written Opinion dated Jul. 21, 2020 for International Patent Application No. PCT/US2020/028505, 9 pages.

3rd Chinese Office Action dated Apr. 1, 2020 for Chinese Patent Application No. 201680048579.6, 8 pages.

Japanese Office Action dated Jun. 18, 2019 for Japanese Application No. 2018509824, 12 pages.

International Search Report and Written Opinion issued in Application No. PCT/US2016/047235 dated Oct. 28, 2016, 11 pages.

Supplemental European Search Report dated Oct. 30, 2020 for European Patent Application No. 18753982, 2 pages.

\* cited by examiner

WIRELESS IMAGING SYSTEM COMPRISING A HEAD UNIT AND A LIGHT CABLE THAT COMPRISES AN INTEGRATED LIGHT SOURCE

CROSS REFERENCE TO RELATED APPLICATIONS

This application is a continuation of U.S. patent application Ser. No. 16/321,337, filed Jan. 28, 2019, which is a U.S. national stage of International Application No. PCT/US2018/018172, filed Feb. 14, 2018, which claims the benefit of U.S. Provisional Application No. 62/459,306, filed Feb. 15, 2017, which are each incorporated by reference herein in its entirety.

FIELD OF THE INVENTION

The invention relates to medical imaging systems, and more particularly to wireless medical imaging systems comprising (a) a head unit comprising: (i) a head unit case; (ii) a head unit electrical connector; (iii) an image sensor; (iv) a wireless transceiver; (v) a central processing unit; and (vi) a user-input component; and (b) a light cable comprising: (i) a light cable electrical connector, (ii) a power cable; and (iii) an integrated light source, wherein the integrated light source comprises: (1) an emissive radiation source having a first spectrum; (2) an optical element located to direct emissions from the emissive radiation source; (3) a volumetric spectrum converter, the converter being located to convert emissions directed from the emissive radiation source to emissions having a second spectrum different from the first spectrum; (4) an optical reflector located about the converter, and (5) an output filter, the reflector being located to reflect the converter emissions towards the output filter, and the integrated light source being configured to transmit light from the light cable through the output filter, for use, for example, with endoscopes, arthroscopes, and other surgical optical imaging instruments and systems.

BACKGROUND OF THE INVENTION

Endoscopic surgery involves using a complex optical instrument system in a minimally invasive surgical procedure to visualize the interior of a hollow organ or cavity in a patient's body, such as, for example, inside of a joint, the respiratory tract, the epidural space, etc. Endoscopic procedures are performed for a variety of reasons including diagnostic examination, cauterization, reconstruction, and ligament repair, among others. These procedures can be performed in hospitals, surgical centers, outpatient centers, or physician offices, and are now being adopted for diagnostic field work, including use by the military.

Endoscopic surgery was first developed in the early 1800s and has steadily, but slowly, evolved over time. The first procedures involved using a small tube and lens, i.e. a simple endoscope, inserted into a patient, through which the physician looked while using candlelight for illumination. While these first procedures were revolutionary and significantly expanded medical understanding of the human body, the procedures were fraught with complications and technological limitations.

The need for illumination has been a critical challenge from the inception of endoscopic surgery. Beginning with candles, the light source has presented many difficulties relating to, for example, ease of use, risk of fire, and low light output, among others. As technology advanced, better light sources were introduced, starting with rudimentary electric lights. Although the industry has progressed to modern lighting methods such as xenon and LEDs, these difficulties have persisted.

Another primary challenge for endoscopy has been how physicians visualize the procedure. The first endoscopes were handheld and required a surgeon to have a direct line of sight into and down the length of the scope. While this allowed the surgeon to clearly view the surgical site, it meant that the surgeon was required to maintain a very precise position in order to use the scope. In addition, the need to maintain sight through the scope meant that the surgeon would have a difficult time using the other tools required for effective or complex surgery, as the surgeon would have to manipulate the tools without seeing where the tools were. However, as with light sources, the technology relating to use of scopes has continued to improve, including advances in optical science and adoption of new manufacturing techniques such a fiber optics and precision rod-lenses. Most recently, the advent of inexpensive and accurate image camera sensors have again dramatically shifted the way endoscopic procedures are performed. The use of digital cameras and external displays allows the surgeon to use an endoscope without having to look straight through the lens, but even more so these developments provided for a much greater amount of control and flexibility while conducting minimally invasive surgery.

Current state-of-the-art endoscopic surgical equipment systems are based on the integration of a series of technological improvements developed over the years. These systems include a camera head unit connected to an endoscope, a powered surgical instrument such as a shaver or an ablator, and an endoscopy cart supporting multiple smart devices including, for example, a light source unit, a camera control unit, a color printer, a patient data management device, a surgical instrument control system, a fluid management system and pump, multiple power sources, digital monitors, and several cables for power and data transmission. There are also at least two major cables connecting the endoscopy cart to the camera head unit and endoscope: one cable that transmits light from the light source through an external fiber optic light cable pathway to the endoscope, and another cable that transmits power and data signals to and from the camera head unit.

Modern endoscopic surgical procedures, which are generally considered quick and simple, actually require a lengthy preoperative period to set up the necessary equipment and require the use of a number of wires and cables that are often draped over patients and can hinder surgeons and their staff. Moreover, although state-of-the-art LED-based systems are more efficient than the older xenon lighting systems, which may use over 1000 watts of power, these newer light source units are still very power intensive, requiring 300 watts or more, most of which is wasted as heat or lost through light leaking from the external light cable. In addition, the wasted heat has been repeatedly cited as the source of operating room fires in cases where the cables were draped over a patient incorrectly or when the heated endoscope met a combustible material.

Thus, there is a need for wireless medical imaging systems that address these issues of energy efficiency, usability, versatility, and safety.

BRIEF SUMMARY OF THE INVENTION

A wireless medical imaging system is provided. The wireless medical imaging system comprises (a) a head unit comprising: (i) a head unit case; (ii) a head unit electrical connector, (iii) an image sensor; (iv) a wireless transceiver; (v) a central processing unit; and (vi) a user-input component. The wireless medical imaging system also comprises (b) a light cable comprising: (i) a light cable electrical connector; (ii) a power cable; and (iii) an integrated light source. The head unit case has an external surface defining an external cavity, an internal surface defining an internal cavity, a first aperture, and a second aperture. The head unit electrical connector is configured to operatively connect with the light cable electrical connector through the first aperture. The light cable electrical connector, the power cable, and the integrated light source are operatively connected in series. The integrated light source comprises: (1) an emissive radiation source having a first spectrum; (2) an optical element located to direct emissions from the emissive radiation source; (3) a volumetric spectrum converter, the converter being located to convert emissions directed from the emissive radiation source to emissions having a second spectrum different from the first spectrum; (4) an optical reflector located about the converter; and (5) an output filter, the reflector being located to reflect the converter emissions towards the output filter, and the integrated light source being configured to transmit light from the light cable through the output filter. The image sensor, the wireless transceiver, and the central processing unit are disposed within the internal cavity. The image sensor is configured to detect an image transmitted into the head unit through the second aperture. The external cavity is configured to receive an external battery. The user-input component is disposed on the external surface.

In some examples, the integrated light source comprises a solid state light source that can produce continuous spectrum light; and/or output of the integrated light source has a spectral bandwidth that is nominally 480 nm to 775 nm. Also in some examples, the emissive radiation source operates in the range of 400 nm to 480 nm. Also in some examples, the optical element may either collimate, convergently focus, or divergently focus the emissive radiation source emissions onto the converter. Also in some examples, the optical reflector redirects omnidirectional light into a desired optical path. Also in some examples, the converter converts the emissions from the emissive radiation source to emissions of different wavelength, a narrower spectrum, or a broader spectrum, of non-coherent radiation. Also in some examples, the filter eliminates an emission from the emissive radiation source that has not been converted by the converter as well as optionally further conditioning the emitted light. Also in some examples, the emissive geometry of the emitted radiation spectrum from the integrated light source may be further conditioned, directed, focused, collimated, reflected, refracted, diffracted, or otherwise modified with the inclusion of suitable optical components.

In some examples, the integrated light source is configured to provide illumination to an area of interest by connection of the light cable to a medical imaging scope, such that the light is transmitted from the integrated light source, into the medical imaging scope, to the area of interest. In some embodiments of these examples, the light cable further comprises a protective housing, the protective housing surrounds the integrated light source and has an opening, and the integrated light source is configured to transmit light from the light cable through the opening. Also in some embodiments of these examples, the light cable further comprises an adaptor configured to make the connection of the light cable to the medical imaging scope. Also in some embodiments of these examples, the adaptor is built into the protective housing, to allow for an integrated design. Also in some embodiments of these examples, the adaptor is further configured to allow rotation of the adaptor and the light cable with respect to the medical imaging scope while the light cable is connected to the medical imaging scope.

In some examples, the light cable further comprises a flexible sheath that surrounds the power cable. Also in some examples, the light cable does not comprise a fiber optic cable. Also in some examples, the image sensor comprises a complementary metal-oxide-semiconductor (CMOS) chip, a scientific complementary metal-oxide-semiconductor (sCMOS) chip, a charge-coupled device (CCD) chip, or a combination thereof.

In some examples, the wireless transceiver of the head unit is configured to transmit and receive image sensor data and command and control signals, both to and from a wireless transceiver of a remote receiver unit. Also in some examples, the head unit is configured to establish a connection between the wireless transceiver of the head unit and the wireless transceiver of the remote receiver unit when the head unit and the remote receiver unit are located as far as 30 meters from each other. Also in some examples, the wireless transceiver of the head unit may use the ultra-wideband (UWB) communication modality. Also in some examples, the wireless transceiver of the head unit is configured to transmit data from the image sensor and command and control signals to an external system for management of medical imaging systems without need for reprogramming or redesign.

In some examples, the central processing unit manages at least one of the integrated light source, the image sensor, or the wireless transceiver. Also in some examples, the head unit further comprises a coprocessor that assists the image sensor in converting the image for the central processing unit. Also in some examples, the user-input component comprises buttons configured to control functions of the image sensor. Also in some examples, the second aperture comprises a second aperture connector configured for connection of a medical imaging scope to the head unit case.

In some examples, the head unit case has a volume of 300 to 800 cm$^3$. Also in some examples, the head unit electrical connector and the image sensor are disposed within 1 to 6 cm from each other. Also in some examples, the head unit does not comprise a heat sink within the internal cavity of the head unit. Also in some examples, the head unit further comprises a window, the window being disposed within the second aperture and configured to allow the image to pass therethrough.

In some examples, the wireless medical imaging system further comprises an external battery that is disposed in the external cavity and that provides power to one or more of the integrated light source, the image sensor, the wireless transceiver, or the central processing unit. In some embodiments of these examples, the external battery is a removable rechargeable battery. In some of these embodiments, the wireless medical imaging system further comprises a removable housing for the removable rechargeable battery, the removable housing comprising the removable rechargeable battery, and the external cavity being configured to receive the removable rechargeable battery via latching of the removable housing into the external cavity. Also in some of these embodiments, the removable housing further comprises a battery management system. Also in some of these embodiments, the battery management system is configured to (a) regulate power output from the removable rechargeable battery, (b) report charge level of the removable rechargeable battery, and (c) protect against faults. Also in some embodiments of these examples, the external battery is a non-removable rechargeable battery. Also in some embodiments of these examples, the external battery has a high capacity and can provide adequate power to operate the integrated light source, the image sensor, and the wireless transceiver. In some of these embodiments, the external battery has a capacity above 3,000 milliampere hours (mAh). Also in some embodiments of these examples, the head unit further comprises a power management system that is configured to control power supplied by the external battery and to distribute the power to the one or more of the integrated light source, the image sensor, the wireless transceiver, or the central processing unit.

In some examples, the wireless medical imaging system further comprises a remote receiver unit. In accordance with these examples, the remote receiver unit comprises: (i) a receiver unit case; (ii) a wireless transceiver; (iii) a central processing unit; and (iv) a communications interface. Also, the receiver unit case has an internal cavity that contains the wireless transceiver of the remote receiver unit, the central processing unit of the remote receiver unit, and the communications interface. In some embodiments of these examples, the wireless transceiver of the remote receiver unit is configured to transmit and receive image sensor data and command and control signals, both to and from the wireless transceiver of the head unit. Also in some embodiments of these examples, the central processing unit of the remote receiver unit manages one or more of the wireless transceiver of the remote receiver unit or the communications interface and can perform data processing therefor. Also in some embodiments of these examples, the communications interface is configured to communicate with multiple types of external camera management systems without need for reprogramming or redesign.

In some examples, the head unit further comprises an internal rechargeable battery. In accordance with these examples, the internal cavity further contains the internal rechargeable battery. In some embodiments of these examples, the internal rechargeable battery is configured to be used as a secondary battery system in case an external battery ceases to provide power or is disconnected. Also in some embodiments of these examples, the head unit further comprises a battery management system configured to manage the internal rechargeable battery. In some of these embodiments, the internal rechargeable battery and the battery management system of the head unit allow the integrated light source, the image sensor, the wireless transceiver, and the central processing unit to switch to a lower power mode in order to conserve power. Also in some embodiments of these examples, the internal rechargeable battery can be charged to capacity from an external battery. Also in some examples of these embodiments, the internal rechargeable battery is configured to be controlled externally by a separate power or battery management system depending on the presence of an external battery. Also in some embodiments of these examples, the internal rechargeable battery is sufficient to provide power for operation of the wireless medical imaging system.

BRIEF DESCRIPTION OF THE DRAWINGS

Referring now to the drawings in which like reference numbers represent corresponding parts throughout.

DETAILED DESCRIPTION OF THE INVENTION

In the following description, various embodiments of a wireless medical imaging system are described. It is to be understood that other embodiments may be used and that structural changes may be made without departing from the scope of the wireless medical imaging system. Also, it is to be understood that unless otherwise indicated the wireless medical imaging system is not limited to particular materials, dimensions, manufacturing processes, or the like, as such may vary.

Figure 6:
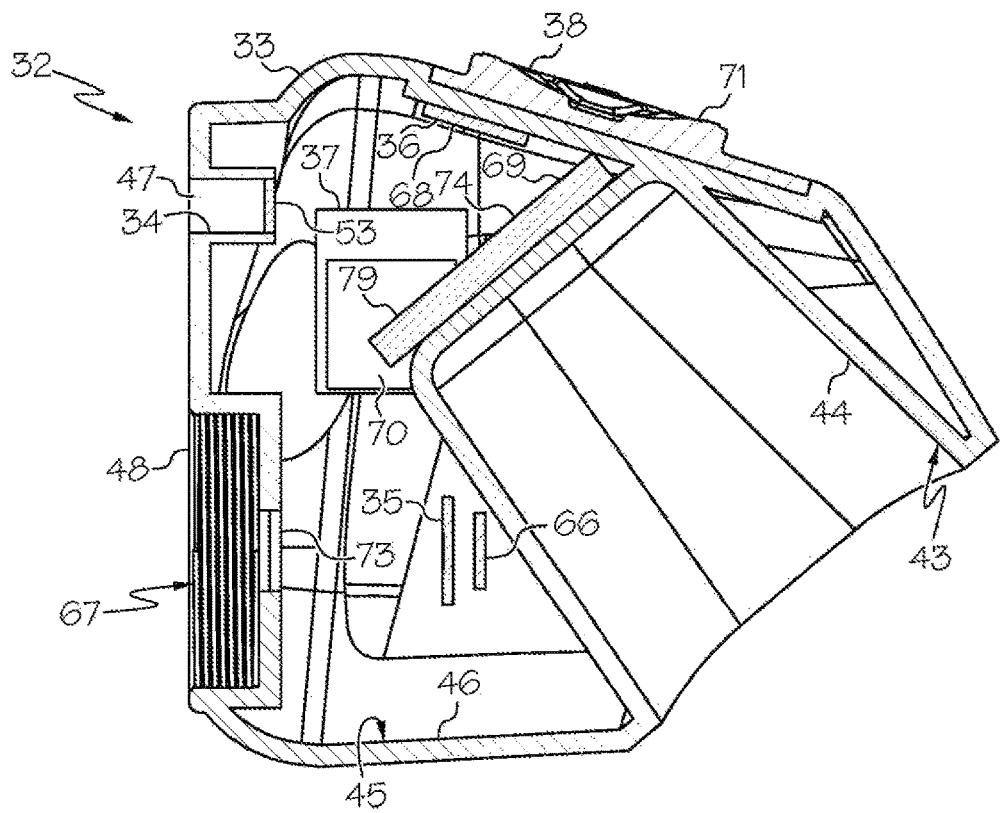
FIG. 6 shows an embodiment of the head unit of FIG. 3, in sectional view.
Figure 23:
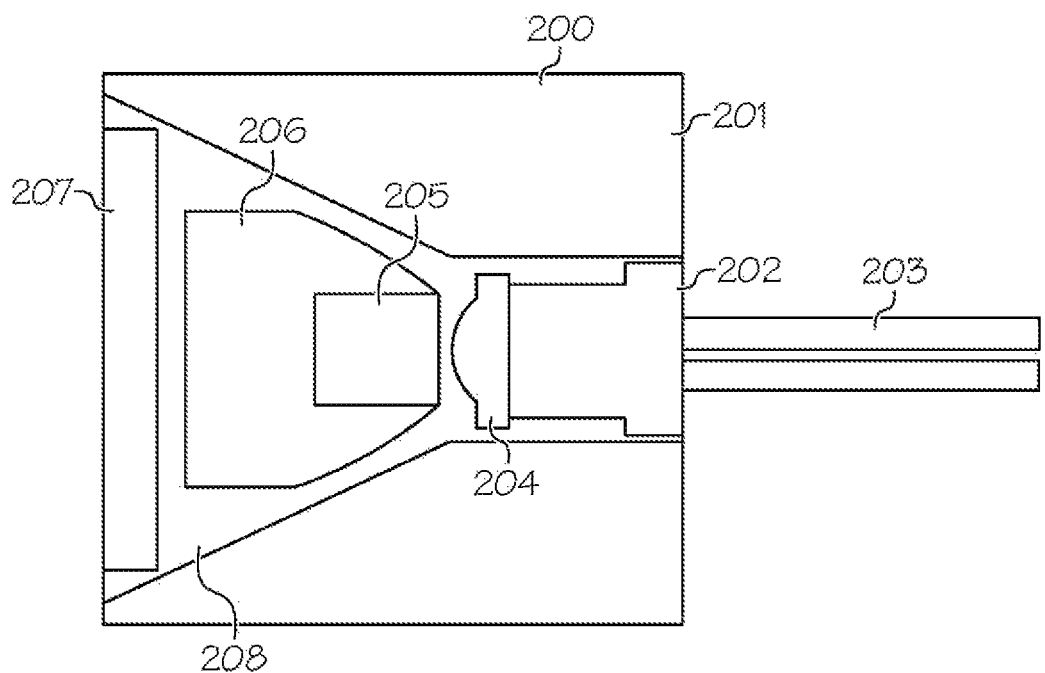
FIG. 23 is a schematic diagram of another integrated light source that uses multiple parts to enhance the efficiency and safety of the light source, as disclosed herein.

As shown in the FIGS. 1-21 and FIG. 23, a wireless medical imaging system 31 is disclosed. As shown in FIGS. 1-6, the wireless medical imaging system 31 comprises (a) a head unit 32 comprising: (i) a head unit case 33; (ii) a head unit electrical connector 34; (iii) an image sensor 35; (iv) a wireless transceiver 36; (v) a central processing unit 37; and (vi) a user-input component 38. As shown in FIG. 1 and FIGS. 8-11, the wireless medical imaging system 31 also comprises (b) a light cable 39 comprising: (i) a light cable electrical connector 40; (ii) a power cable 41; and (iii) an integrated light source 42. As shown in FIG. 3 and FIG. 6, the head unit case 33 has an external surface 43 defining an external cavity 44, an internal surface 45 defining an internal cavity 46, a first aperture 47, and a second aperture 48. As shown in FIG. 10, the head unit electrical connector 34 is configured to operatively connect with the light cable electrical connector 40 through the first aperture 47. The light cable electrical connector 40, the power cable 41, and the integrated light source 42 are operatively connected in series. As shown in FIG. 11 and FIG. 23, the integrated light source 42 comprises: (1) an emissive radiation source 202 having a first spectrum; (2) an optical element 204 located to direct emissions from the emissive radiation source 202; (3) a volumetric spectrum converter 205, the converter 205 being located to convert emissions directed from the emissive radiation source 202 to emissions having a second spectrum different from the first spectrum; (4) an optical reflector 206 located about the converter 205; and (5) an output filter 207, the reflector 206 being located to reflect the converter 205 emissions towards the output filter 207, and the integrated light source 42 being configured to transmit light from the light cable 39 through the output filter 207. As shown in FIG. 6, the image sensor 35, the wireless transceiver 36, and the central processing unit 37 are disposed within the internal cavity 46. The image sensor 35 is configured to detect an image transmitted into the head unit 32 through the second aperture 48. As shown in FIG. 10, the external cavity 44 is configured to receive an external battery 49. The user-input component 38 is disposed on the external surface 43.

Figure 1:
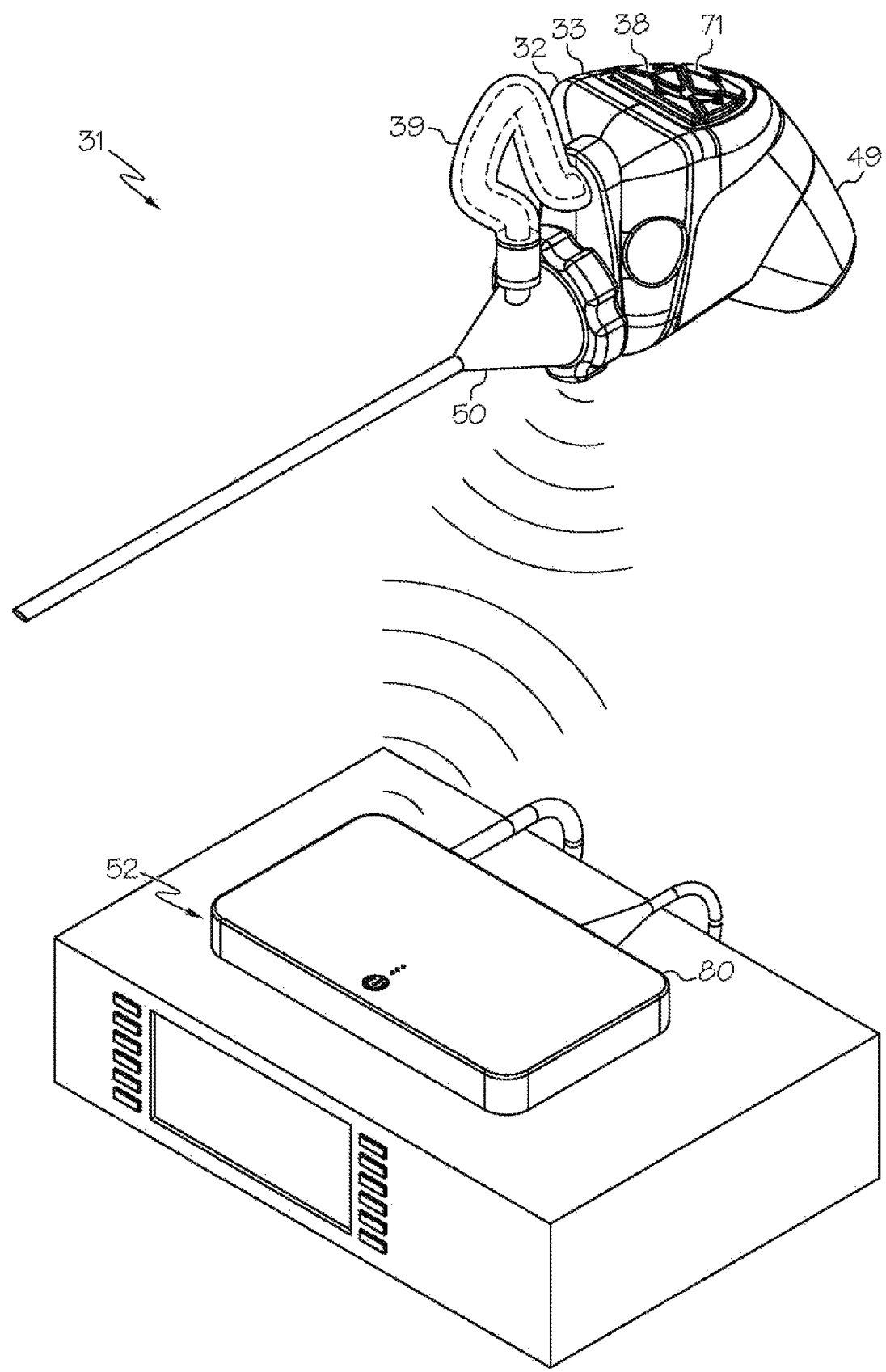
FIG. 1 shows an exemplary wireless medical imaging system as disclosed herein, in this example comprising a head unit, a light cable, a removable housing comprising a removable rechargeable battery, and a remote receiver unit, wherein the removable housing comprising the removable rechargeable battery is attached to the head unit, the head unit is attached to a medical imaging scope corresponding to an endoscope, and the remote receiver unit is attached to a state-of-the-art endoscopy system, in perspective view.
Figure 9:
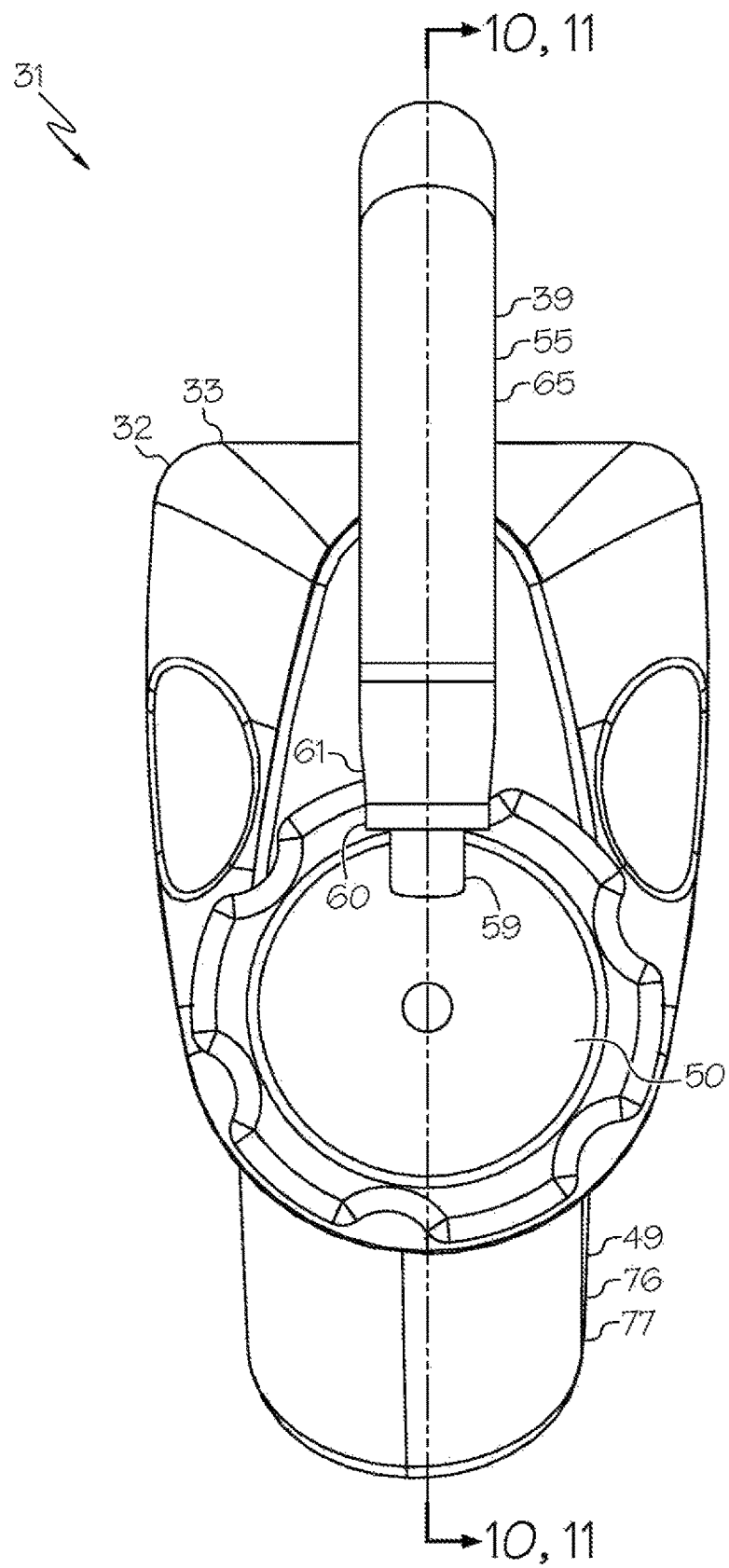
FIG. 9 shows the head unit, the light cable, and the removable housing comprising the removable rechargeable battery of the exemplary wireless medical imaging system of FIG. 1, wherein the removable housing comprising the removable rechargeable battery is attached to the head unit, and the head unit is attached to a medical imaging scope corresponding to an endoscope, in front view.
Figure 10:
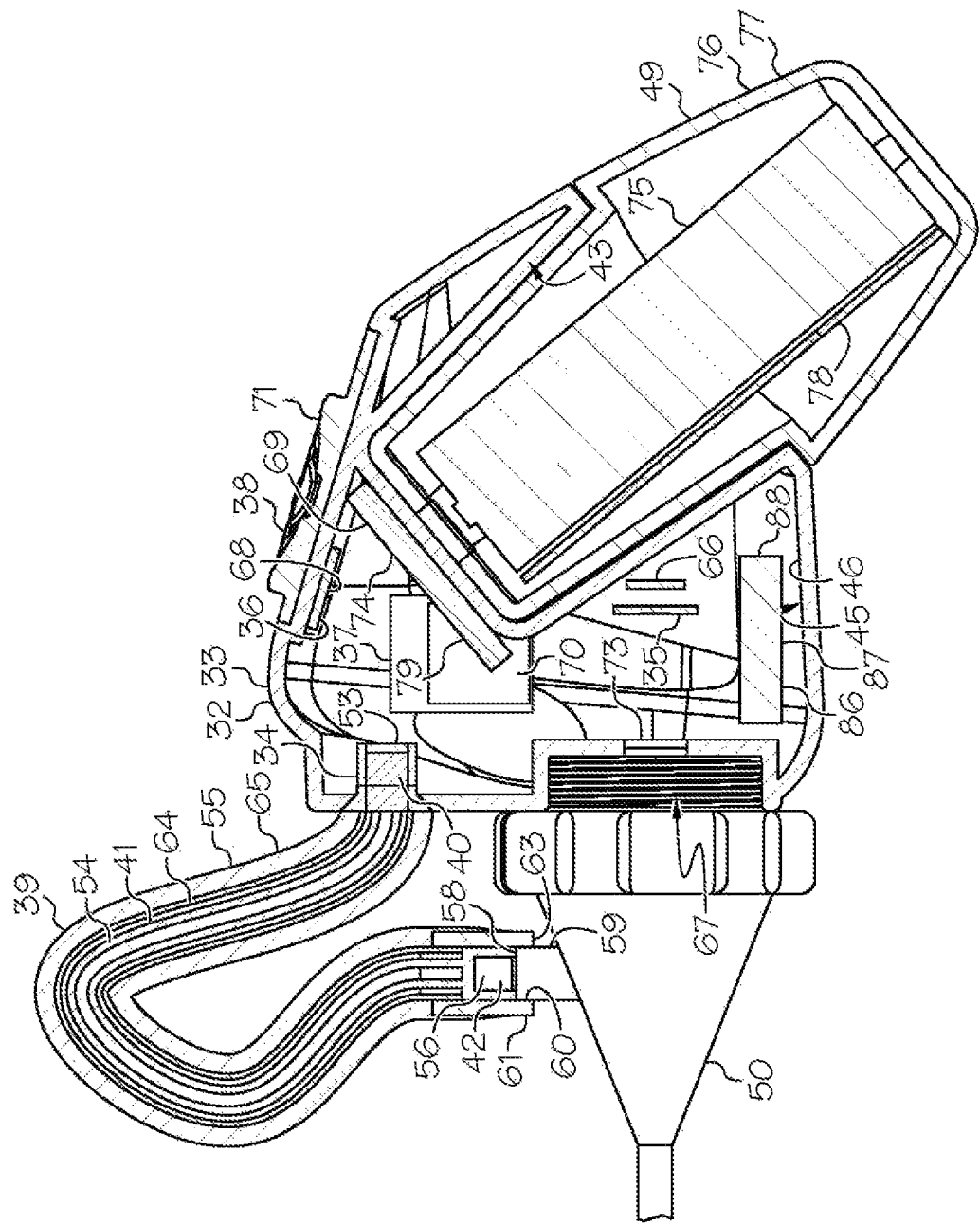
FIG. 10 shows the head unit, the light cable, and the removable housing comprising the removable rechargeable battery of the exemplary wireless medical imaging system of FIG. 9, wherein the head unit further comprises an internal rechargeable battery, the removable housing comprising the removable rechargeable battery is attached to the head unit, and the head unit is attached to a medical imaging scope corresponding to an endoscope (the endoscope is only partially shown), in sectional view.
Figure 11:
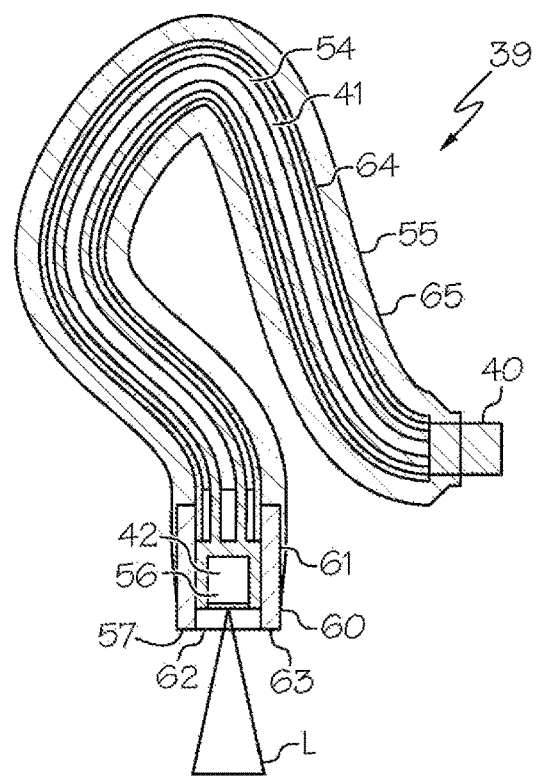
FIG. 11 shows the light cable of FIG. 9, in sectional view, and transmitted light (L)
Figure 12:
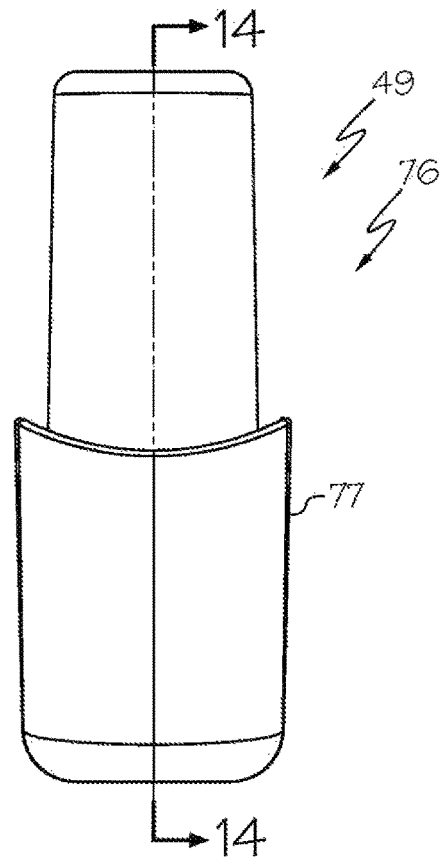
FIG. 12 shows the removable housing comprising the removable rechargeable battery of the exemplary wireless medical imaging system of FIG. 1, in front view.
Figure 13:
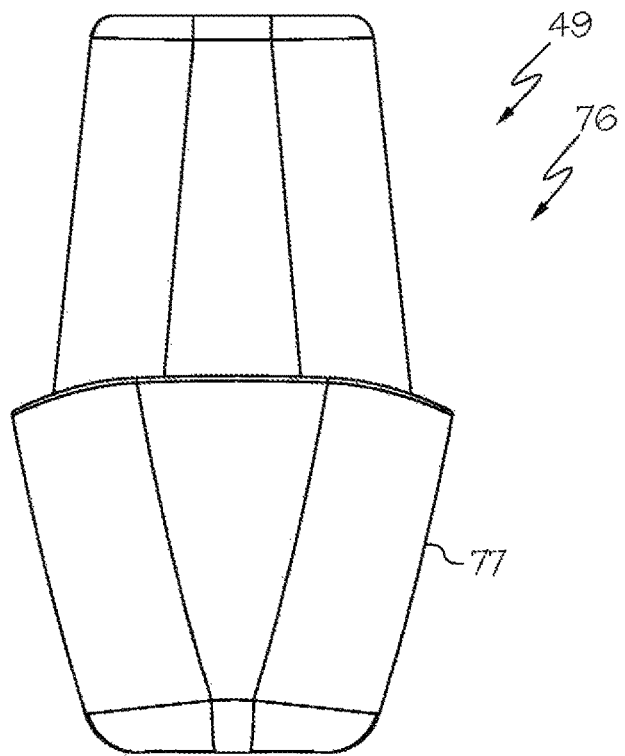
FIG. 13 shows the removable housing comprising the removable rechargeable battery of FIG. 12, in side view.
Figure 14:
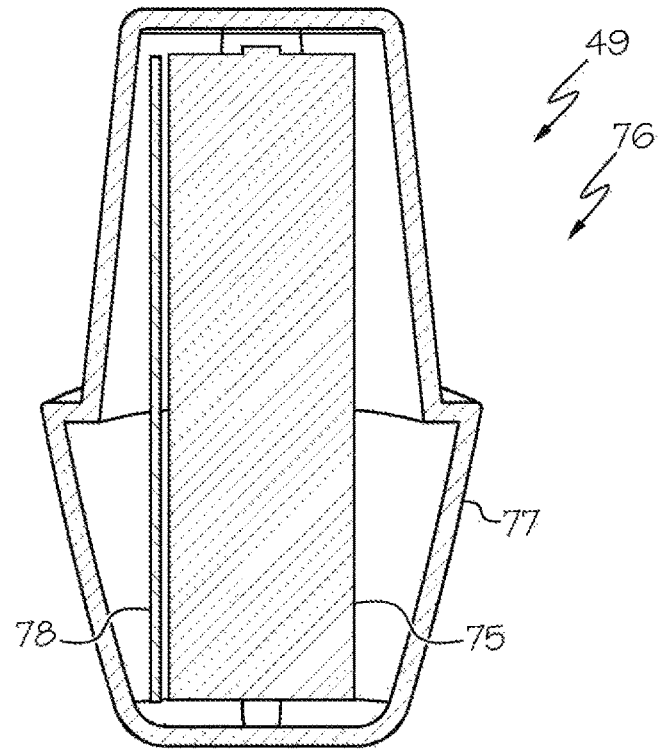
FIG. 14 shows an embodiment of the removable housing comprising the removable rechargeable battery of FIG. 12, in sectional view.
Figure 15:
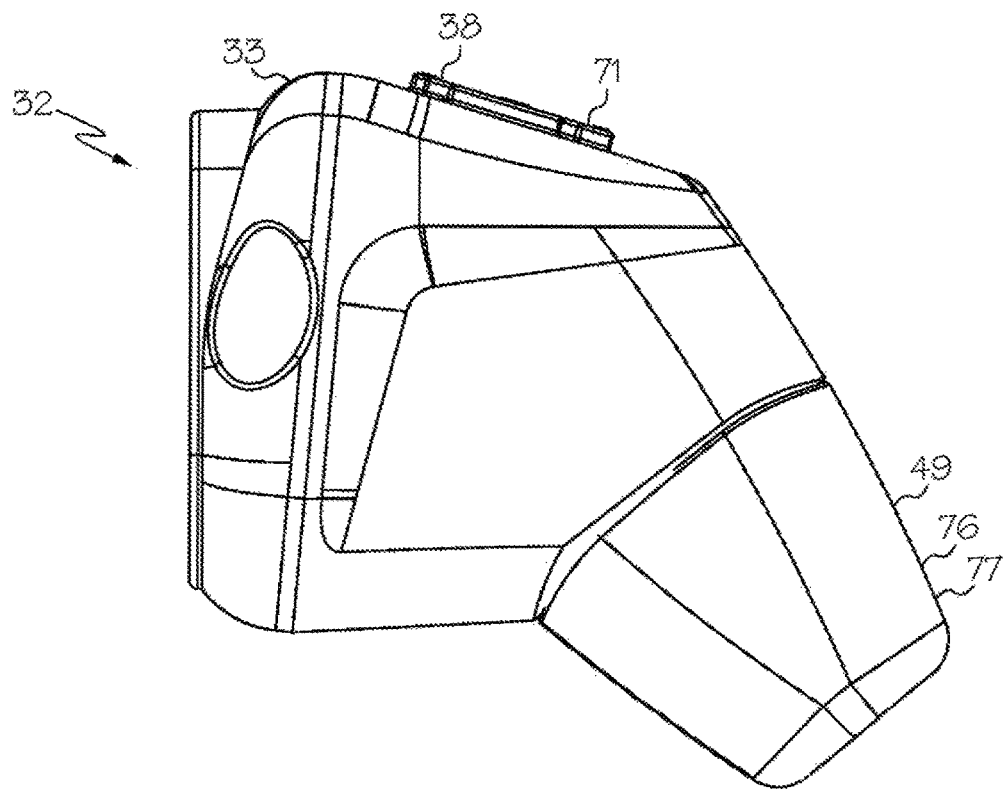
FIG. 15 shows the head unit and the removable housing comprising the removable rechargeable battery of FIG. 1, with the removable housing comprising the removable rechargeable battery being attached to the head unit, in side view.
Figure 16:
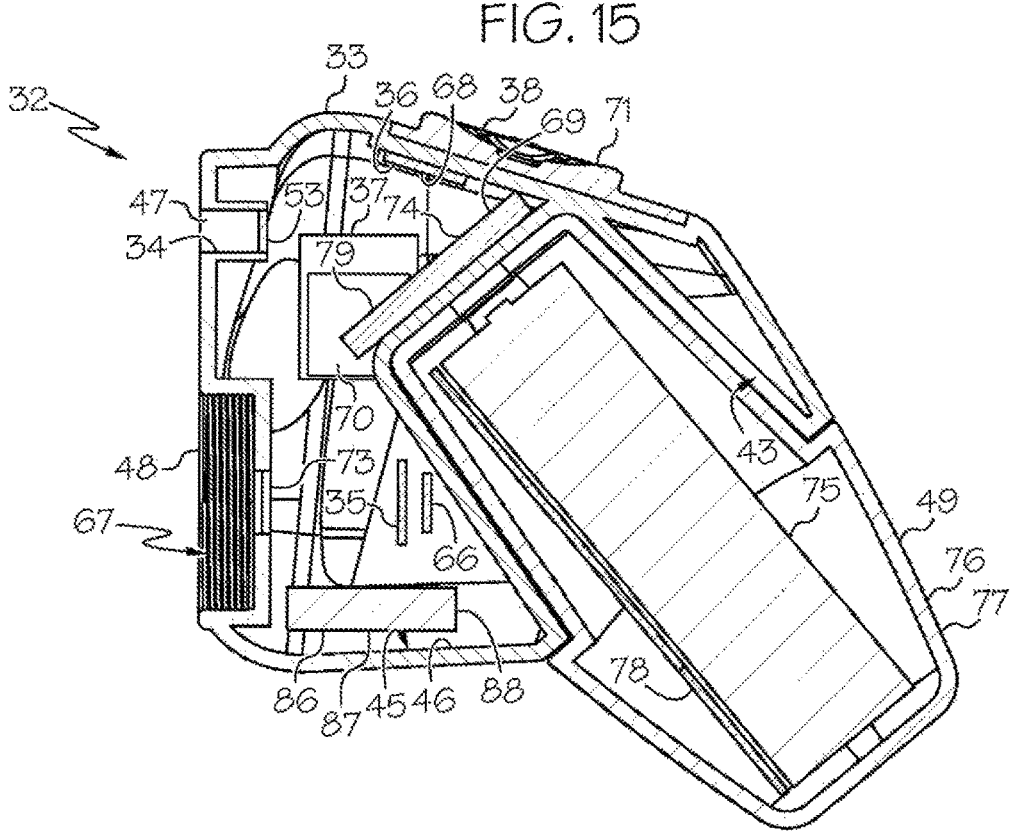
FIG. 16 shows an embodiment of the head unit of FIG. 3, wherein the head unit further comprises an internal rechargeable battery, and with the removable housing comprising the removable rechargeable battery of FIG. 12 being attached to the head unit, in sectional view.
Figure 21:
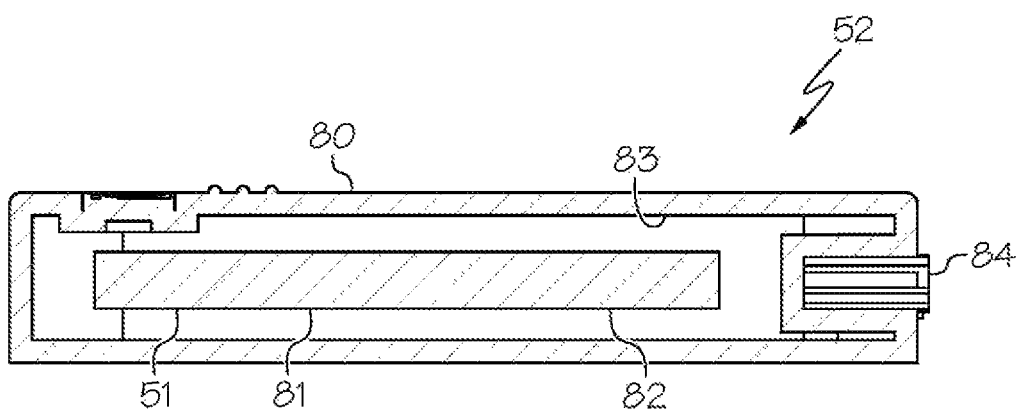
FIG. 21 shows the remote receiver unit of FIG. 19, in sectional view.

As shown in FIG. 1, FIG. 9, and FIG. 10, the wireless medical imaging system 31 can be operated as follows. The head unit 32 and the light cable 39 can be connected, based on operative connection of the head unit electrical connector 34 with the light cable electrical connector 40. The light cable 39 can be connected to a medical imaging scope 50, e.g. an endoscope, an arthroscope, or another medical imaging scope. The medical imaging scope 50 also can be connected to the head unit 32, e.g. at the second aperture 48 of the head unit 32. The head unit 32 can supply power to the integrated light source 42 from a battery, e.g. an external battery and/or an internal battery, through the head unit electrical connector 34, the light cable electrical connector 40, and the power cable 41. The integrated light source 42 can provide illumination to an area of interest, e.g. a surgical site within a human or animal patient, such that the light is transmitted from the integrated light source 42, into the medical imaging scope 50, to the area of interest. The image sensor 35 can then detect an image transmitted into the head unit 32 through the second aperture 48. As shown in FIG. 1, FIG. 10, and FIG. 21, the wireless transceiver 36 of the head unit 32 can transmit and receive image sensor data and command and control signals, e.g. both to and from a wireless transceiver 51 of a remote receiver unit 52. The user-input component 38 can be used to control the integrated light source 42 and/or the image sensor 35.

Considering the head unit 32 first, with reference to FIG. 10, as noted the wireless medical imaging system 31 comprises (a) a head unit 32 comprising: (i) a head unit case 33; (ii) a head unit electrical connector 34; (iii) an image sensor 35; (iv) a wireless transceiver 36; (v) a central processing unit 37; and (vi) a user-input component 38.

The head unit case 33 can be made by molding, casting, and/or 3D printing, among other techniques. The head unit case 33 can be made of materials such as, for example, plastic, stainless steel, and/or titanium, among others. The head unit case 33 can serve as a housing for the image sensor 35, the wireless transceiver 36, and the central processing unit 37, for example, providing protection during use, e.g. during surgery, and during cleaning, e.g. during sterilization. The head unit case 33 also can serve as a structure on which the external battery 49 can be received, for example providing a site of attachment, support, and/or quick replacement of the external battery 49 during use, e.g. during surgery.

The head unit electrical connector 34 can be a standard electrical connector, e.g. a plug or socket component of a plug and socket connector, or a custom electrical connector, among other types. The head unit electrical connector 34 can be operatively connected to a battery, e.g. an external battery and/or an internal battery. The head unit electrical connector 34 also can be operatively connected to a light source driver 53, as discussed below. Suitable head unit electrical connectors 34 include, for example, pin-socket connectors, precision gas tight coupling connectors, Mill-Max connectors, single-pin+ boot connectors, MT connection connectors, feed-through pin connectors, barrel-type connectors, spring loaded (pogo) connectors, and contact connectors.

Turning to the light cable 39, again with reference to FIG. 10, as noted the wireless medical imaging system 31 also comprises a light cable 39 comprising: (i) a light cable electrical connector 40; (ii) a power cable 41; and (iii) an integrated light source 42. The light cable 39 can be custom made from standard electrical connectors and power cables that are available from various manufacturers, along with a custom integrated light source 42 as described below. The light cable 39 also can be modified with a variety of enhancements e.g. increased durability, ease of sterilization, etc.

The light cable electrical connector 40, the power cable 41, and the integrated light source 42 are operatively connected in series. Thus, the light cable 39 can supply power to the integrated light source 42 through the light cable electrical connector 40 and the power cable 41.

The light cable electrical connector 40 can be a standard electrical connector, e.g. a plug or socket component of a plug and socket connector, or a custom electrical connector, among other types. As noted, the head unit electrical connector 34 is configured to operatively connect with the light cable electrical connector 40 through the first aperture 47. The operative connection can create an electrical circuit, connecting the integrated light source 42 of the light cable 39 with a battery, e.g. an external battery and/or an internal battery. The operative connection can be direct, e.g. based on the head unit electrical connector 34 and the light cable electrical connector 40 corresponding to a pair of mating electrical connectors, e.g. a plug and socket connector pair. The operative connection also can be indirect, e.g. based on the use of an adaptor to connect the head unit electrical connector 34 and the light cable electrical connector 40. The operative connection through the first aperture 47 can be accomplished, for example, based on the head unit electrical connector 34 being disposed within the internal cavity 46 of the head unit 32, and the light cable electrical connector 40 being inserted through the first aperture 47, such that connection of the head unit electrical connector 34 with the light cable electrical connector 40 occurs in the internal cavity 46 of the head unit 32. The operative connection through the first aperture 47 also can be accomplished, for example, based on the head unit electrical connector 34 being disposed on the external surface 43 of the head unit 32, and the head unit electrical connector 34 being operatively connected to a battery, e.g. an external battery or an internal battery, through the first aperture 47, such that connection of the head unit electrical connector 34 with the light cable electrical connector 40 occurs outside of the head unit 32. The operative connection through the first aperture 47 also can be accomplished other ways, e.g. such that connection of the head unit electrical connector 34 with the light cable electrical connector 40 occurs in the first aperture 47 itself. In any case, the operative connection through the first aperture 47 also can be accomplished such that the first aperture 47 is effectively sealed, e.g. based on sealing contact between the light cable 39 and the head unit case 33 at the first aperture 47, upon connection. Like for the head unit electrical connector 34, suitable light cable electrical connectors 40 include, for example, pin-socket connectors, precision gas tight coupling connectors, Mill-Max connectors, single-pin+ boot connectors, MT connection connectors, feed-through pin connectors, barrel-type connectors, spring loaded (pogo) connectors, and contact connectors.

The power cable 41 of the light cable 39 can be a standard power cable, particularly including a conductor 54. Suitable power cables 41 include, for example, copper aluminum, and solid conductors.

As noted above, with reference to FIG. 11 and FIG. 23, the integrated light source 42 comprises: (1) an emissive radiation source 202 having a first spectrum; (2) an optical element 204 located to direct emissions from the emissive radiation source 202; (3) a volumetric spectrum converter 205, the converter 205 being located to convert emissions directed from the emissive radiation source 202 to emissions having a second spectrum different from the first spectrum; (4) an optical reflector 206 located about the converter 205; and (5) an output filter 207, the reflector 206 being located to reflect the converter 205 emissions towards the output filter 207, and the integrated light source 42 being configured to transmit light from the light cable 39 through the output filter 207. Thus, the integrated light source 42 can be a light source for which the various components of the light source have been integrated, e.g. into a one-piece form, as opposed to, for example, a light source for which the various components remain discrete, e.g. remaining readily detachable and/or interchangeable. The integrated light source 42 can be, for example, a light emitting diode, a laser diode, or an organic light emitting diode, among other types of integrated light sources. In some examples, the integrated light source 42 comprises a solid state light source 56 that can produce continuous spectrum light, and/or output of the integrated light source 42 has a spectral bandwidth that is nominally 480 nm to 775 nm. Also in some examples, the integrated light source 42 can produce a spectrum of light that is tunable. Also in some examples, the wireless medical imaging system 31 comprises a plurality of integrated light sources 42. The integrated light source 42 is described in more detail below.

With reference to FIGS. 8-11, in some examples, the integrated light source 42 is configured to provide illumination to an area of interest, e.g. a surgical site within a human or animal patient, by connection of the light cable 39 to a medical imaging scope 50, such that the light is transmitted from the integrated light source 42, into the medical imaging scope 50, to the area of interest. For example the integrated light source 42 can be positioned within the light cable 39, or at an end 57 thereof, in an orientation such that the integrated light source 42 transmits light into the medical imaging scope 50, to the area of interest. This can be based, for example, on the connection of an end 57 of the light cable 39 at which the integrated light source 42 is positioned, with an end 58 of a light post 59 of a medical imaging scope 50. The connection can be direct, e.g. by direct contact between the end 57 of the light cable 39 and the end 58 of the light post 59, or indirect, e.g. by use of an adaptor 60 between the end 57 of the light cable 39 and the end 58 of the light post 59, as discussed below.

In some examples, the light cable 39 further comprises a protective housing 61. The protective housing 61 can be, for example, a cylindrical housing, among other shaped housings, and can be made for example, from a metal, such as titanium, among other materials. In accordance with these examples, the protective housing 61 surrounds the integrated light source 42, thereby providing protection to the integrated light source 42, e.g. from damage due to physical contact with other objects, and potentially serving as a heat sink for the integrated light source 42, e.g. by absorbing heat generated by the integrated light source 42 during use. The protective housing 61 also has an opening 62, thereby allowing the integrated light source 42 to transmit light beyond the protective housing 61. In accordance with these examples, the integrated light source 42 is configured to transmit light from the light cable 39 through the opening 62. For example, the integrated light source 42 can be positioned within the protective housing 61 such that when the integrated light source 42 transmits light through the output filter, the light also can pass through the opening 62 of the protective housing 61.

In some examples, the light cable 39 further comprises an adaptor 60 configured to make the connection of the light cable 39 to the medical imaging scope 50. The adaptor 60 can be, for example, an adaptor for a universal end, among other types of adaptors. In accordance with these examples, an end 57 of the light cable 39, such as an end 63 of a protective housing 61 of the light cable 39, can have an adaptor 60 connected thereto, e.g. integrally or by temporary attachment, among other ways. Thus, in some examples the adaptor is built into the protective housing, to allow for an integrated design. Also in some examples, the adaptor is attached to the protective housing temporarily. The use of an adaptor 60 can allow connection of the light cable 39 to a variety of different standard ends of light posts 59 of a variety of different types of medical imaging scopes 50. Suitable adaptors 60 include, for example, adaptors with standard adaptor ends for instrument ends such as ACMI LUXTEC ends, ACMI SNAP-ON FEMALE ends, ACMI-LONG ends, DESIGNS FOR VISION HEADLIGHT ends, PILLING ends, STORZ OLYMPUS ends, LUXTEC ULTRALITE HEADLIGHT ends, LUXTEC HEADLIGHT ends, WOLF MALE ends, WOLF FEMALE DYONICS ends, ZEISS HEADLIGHT ends, and UNIVERSAL ends, and for light source ends such as ACMI LUXTEC ends, ACMI-LONG STRYKER ends, DESIGNS FOR VISIONS ends, OLYMPUS ends, PILLING ends, LUXTEC ULTRALITE ends, STORZ ends, WOLF DYONICS ends, ZEISS-SMALL ends, and UNIVERSAL ends. Suitable adaptors 60 also include, for example, screw-on connectors, magnetic connectors, and spring connectors.

Also in some examples, the adaptor 60 is further configured to allow rotation of the adaptor 60 and the light cable 39 with respect to the medical imaging scope 50 while the light cable 39 is connected to the medical imaging scope 50. Such an adaptor 60 can serve as a rotating connector. Exemplary suitable rotating connectors include pin-and-ring connectors, and two-ring connectors, among others. A pin-and-ring connector can include a central round port and a co-radial ring on one side of the connector, and a central pin and an offset pin on the other side of the connector. The central pin fits into the central port, and the offset pin can then slide along the co-radial ring. These connections are done using metal pins and rings so that electricity can flow regardless of the relative positions of the adaptor 60 and light post 59. The two-ring system is effectively the same, except that the central pin and port are replaced by a second ring that acts in the same way as the first ring.

Also in some examples, the light cable 39 further comprises a flexible sheath 55 that surrounds the power cable 41. The flexible sheath 55 can protect and insulate the power cable 41 of the light cable 39. The flexible sheath 55 can include, for example, an inner metal sheath 64 and outer plastic sheath 65, among other components and structures.

Also in some examples, the light cable 39 does not comprise a fiber optic cable. The use of a light cable 39 that includes a power cable 41 and the integrated light source 42, instead of a fiber optic cable, greatly increases functionality and durability of the light cable 39, as discussed below.

Returning to the head unit 32, with reference to FIG. 10, as noted the image sensor 35 is configured to detect an image transmitted into the head unit 32 through the second aperture 48, e.g. an image transmitted by a medical imaging scope 50 that is connected at the second aperture 48. Suitable image sensors 35 are known and commercially available, e.g. ON Semiconductor AR0230CS. In some examples, the image sensor 35 comprises a complementary metal-oxide-semiconductor (CMOS) chip, a scientific complementary metal-oxide-semiconductor (sCMOS) chip, a charge-coupled device (CCD) chip, or a combination thereof. Also in some examples, the head unit 32 further comprises a coprocessor 66 that assists the image sensor 35 in converting the image for the central processing unit 37. In these examples, the coprocessor 66 can interface with the image sensor 35. For example, the coprocessor 66 can receive input in the form of raw image data from the image sensor 35 and convert the raw image data into a format that is compressible and readable by most common image processing hardware and/or software. Suitable coprocessors 66 are known and commercially available, e.g. ON Semiconductor AP0202AT.

In some examples, the head unit case 33 has a volume of 300 to 800 cm$^3$, e.g. a volume of 350 to 750 cm$^3$, 400 to 700 cm$^3$, 450 to 650 om$^3$, or 500 to 600 om$^3$. Also in some examples, the head unit electrical connector 34 and the image sensor 35 are disposed within 1 to 6 cm from each other within the head unit case 33, e.g. 1.5 to 5.5 cm, 2 to 5 cm, 2.5 to 4.5, or 3 to 4 cm from each other. In accordance with these examples, the head unit case 33 can have a compact shape.

As noted, the light cable 39 comprises the integrated light source 42. Because the light cable 39 includes the integrated light source 42, the light cable 39 does not need to extend from an endoscopy cart, and thus can be short relative to light cables conventionally used in endoscopy. For example, the light cable 39 can have a length of 3 to 30 cm, 4 to 20 cm, or 5 to 15 cm, among other lengths.

With reference to FIG. 3, FIG. 6, and FIG. 10, in some examples the second aperture 48 comprises a second aperture connector 67 configured for connection of a medical imaging scope 50 to the head unit case 33. The second aperture connector 67 can comprise, for example, threads, such that the second aperture 48 corresponds to a threaded cavity. Threads can allow for most common medical imaging scopes to interface correctly, either by themselves or utilizing industry standard C-Mount couplers.

With reference to FIG. 1, FIG. 10, and FIG. 21, the wireless transceiver 36 of the head unit 32 controls and directs signals to be sent from, and received by, the wireless medical imaging system 31. In some examples, the wireless transceiver 36 of the head unit 32 is configured to transmit and receive image sensor data, e.g. video data, and command and control signals, both to and from the wireless transceiver 51 of a remote receiver unit 52, as discussed below. In some embodiments of these examples, the head unit 32 is configured to establish a connection between the wireless transceiver 36 of the head unit 32 and the wireless transceiver 51 of the remote receiver unit 52 when the head unit 32 and the remote receiver unit 52 are located as far as 30 meters apart from each other. Also in some examples, the wireless transceiver 36 of the head unit 32 uses the ultra-wideband (UWB) communication modality. Also in some examples, the wireless transceiver 36 of the head unit 32 is configured to transmit image sensor data and command and control signals to an external medical imaging system or management system without needing any changes such as reprogramming, redesign, or updates. In some examples the wireless transceiver 36 comprises and/or interfaces with an antenna 68. The antenna 68 can allow for transmitting and receiving wireless signals carrying image sensor data and/or command and control signals to and from the remote receiver unit 52 and/or to and from a medical imaging system, e.g. such as a camera control unit on a standard endoscopy cart. Suitable wireless transceivers 36 are known and commercially available, e.g. Starix Technology STXI 101.

As noted above in some examples the head unit case 33 has a volume of 300 to 800 cm$^3$, e.g. a volume of 350 to 750 cm$^3$, 400 to 700 cm$^3$, 450 to 650 cm$^3$, or 500 to 600 cm$^3$. A head unit case 33 having a volume within these ranges can be handheld. Accordingly, the wireless transceiver 36 of the head unit 32 can transmit and receive image sensor data, e.g. video data, and command and control signals, both to and from the wireless transceiver 51 of a remote receiver unit 52, with the head unit 32 being handheld.

With reference to FIG. 10, the central processing unit 37 can perform and/or control one or more functions of the wireless medical imaging system 31. In some examples, the central processing unit 37 manages at least one of the following: the integrated light source 42, the image sensor 35, or the wireless transceiver 36. In some embodiments of these examples, the central processing unit 37 can perform functions such as, for example, encoding video signals from an image sensor 35 as discussed above, decoding transmissions from the wireless transceiver 36, and/or controlling the brightness of the integrated light source 42, among others. Also in some embodiments, the central processing unit 37 can interface with a battery system 69, as discussed below, and distribute power to some or all components of the wireless medical imaging system 31, e.g. the integrated light source 42, the image sensor 35, and/or the wireless transceiver 36, among others. Also in some embodiments, the central processing unit 37 can interface with a memory module 70. The memory module 70 can allow, for example, storage and retrieval of data, instructions, and/or command signals sent by or to some or all of the components of the wireless medical imaging system 31. Also in some embodiments, the central processing unit 37 can interface with a light source driver 53. The light source driver 53 can receive power supplied by the battery system 69 as discussed below and can convert and shape the power in such a way that the integrated light source 42 can be operated efficiently. Suitable central processing units 37 are known and commercially available, e.g. NXP SCM-i.MX 6Dual.

Figure 2:
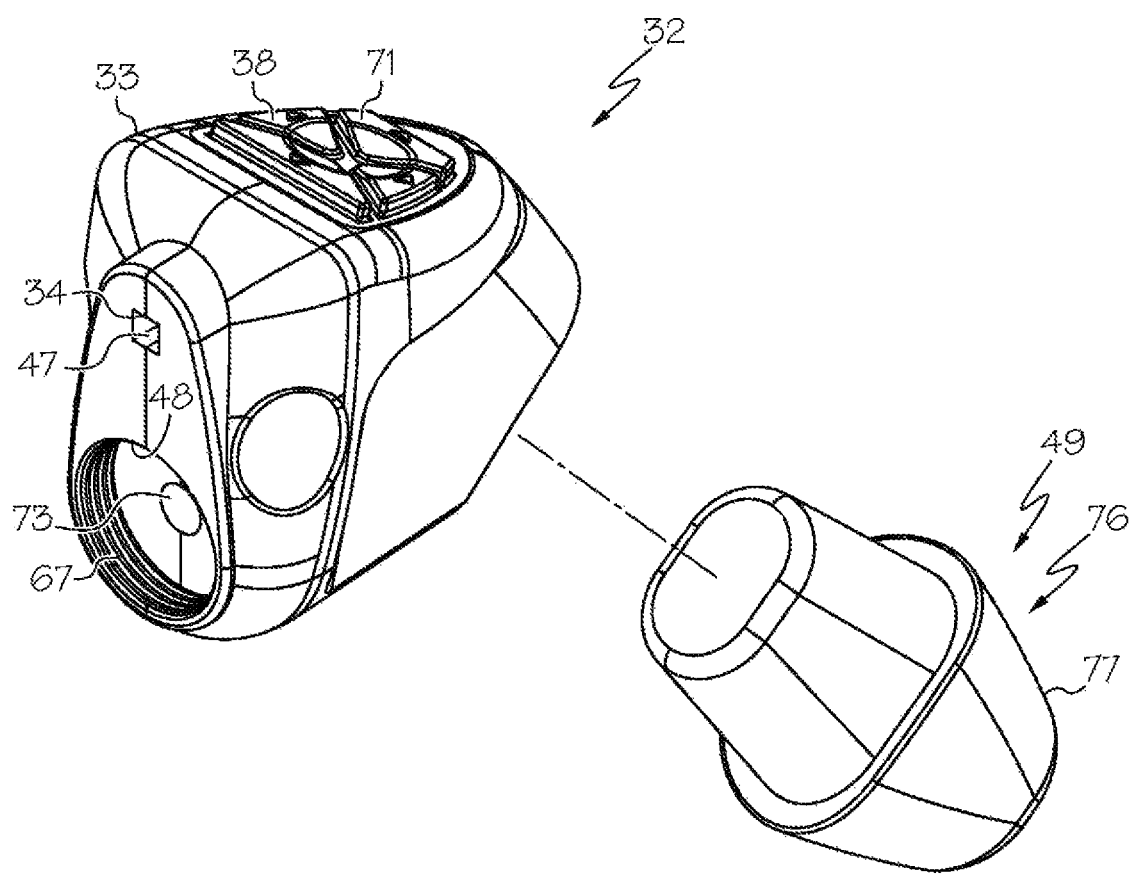
FIG. 2 shows the head unit and the removable housing comprising the removable rechargeable battery of the wireless medical imaging system of FIG. 1, in exploded view, in perspective view.
Figure 3:
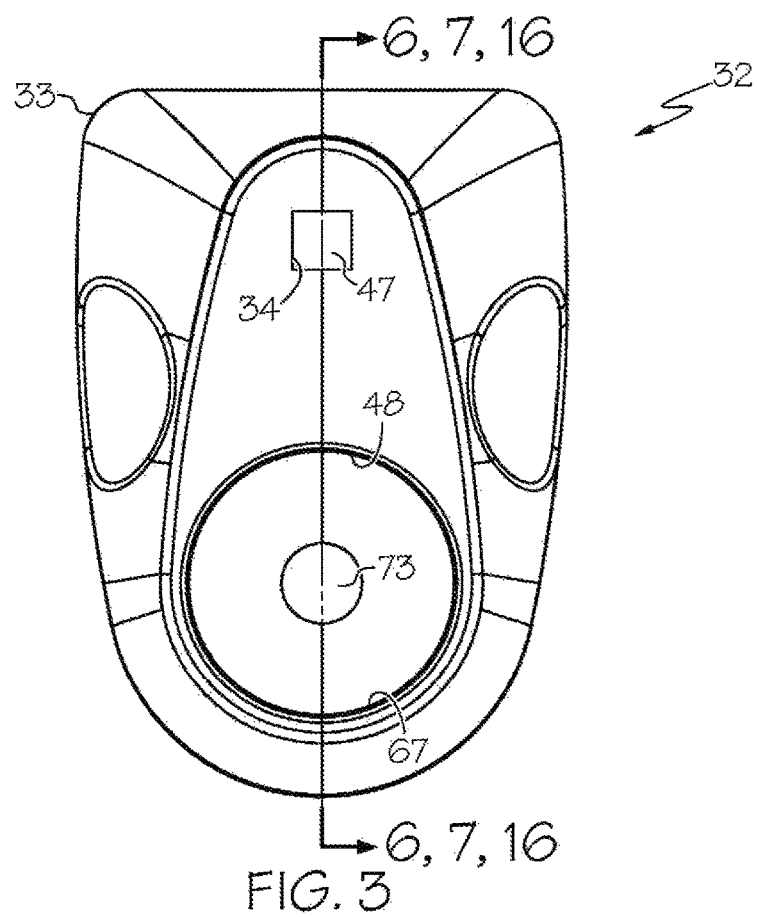
FIG. 3 shows the head unit of the exemplary wireless medical imaging system of FIG. 1, in front view.
Figure 4:
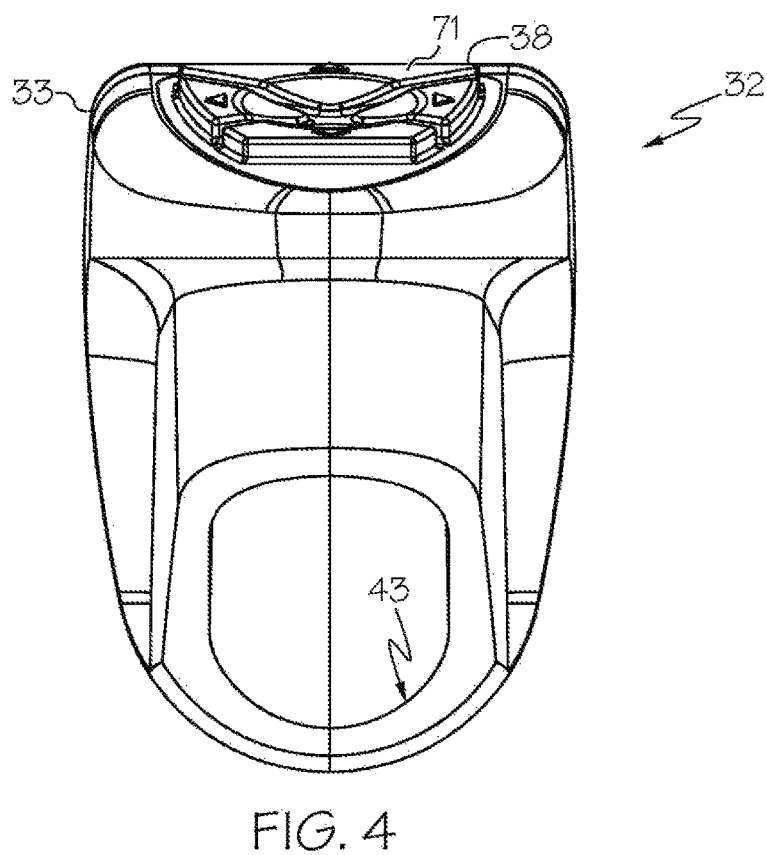
FIG. 4 shows the head unit of FIG. 3, in back view.
Figure 5:
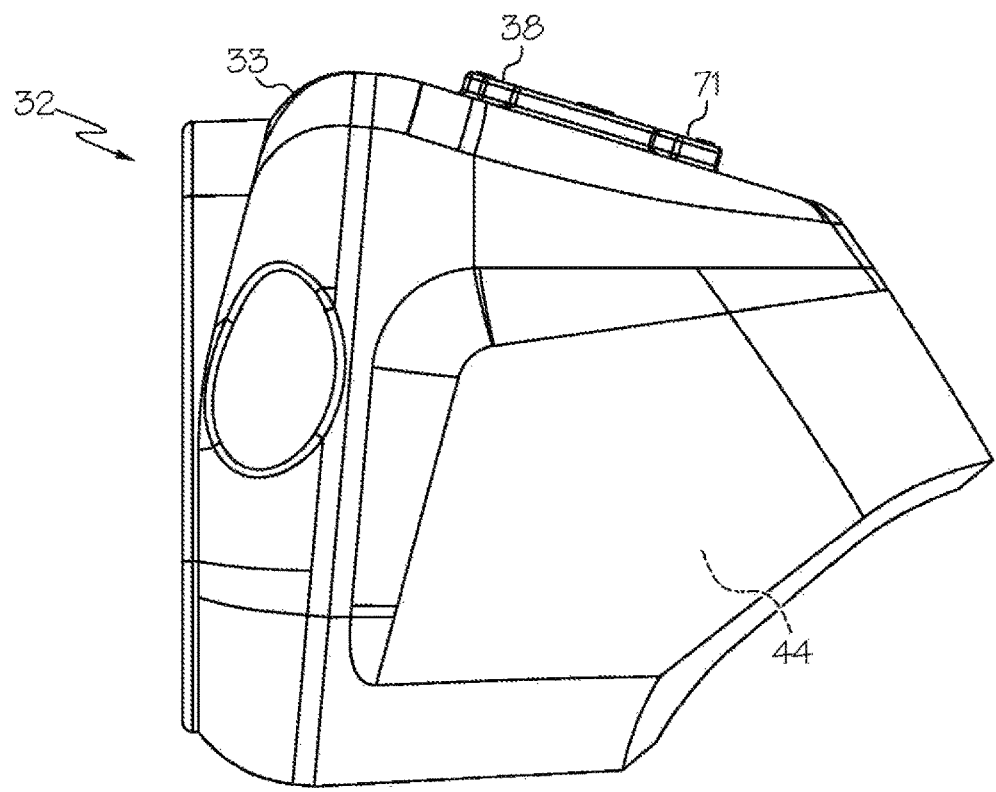
FIG. 5 shows the head unit of FIG. 3, in side view.

With reference to FIG. 1, FIG. 2, and FIG. 10, the user-input component 38 can correspond to a control surface 71 that allows a user to interface with the integrated light source 42 and/or the image sensor 35. The user-input component 38 can comprise, for example, rubber buttons, capacitive buttons, scroll wheels, capacitive screens and/or switches, which can be operatively coupled to the integrated light source 42 and/or the image sensor 35. The interfacing can comprise controlling features of the integrated light source 42, such as for example, power and/or intensity. This can be done, for example, by supplying direct power to a diode of the integrated light source 42 and/or imposing a duty cycle on a diode of the integrated light source 42 that reduces overall power consumption and flickers the diode at a rate faster than be seen by a human eye or a camera. The interfacing also can comprise controlling features of the image sensor 35, such as, for example, white balance, brightness, zoom, and/or image capture, among others.

Thus, in some examples the user-input component 38 comprises buttons configured to control functions of the integrated light source 42.

Also, in some examples the user-input component 38 comprises buttons configured to control functions of the image sensor 35.

With reference to FIG. 10, the head unit 32 can optionally include a heat sink within the internal cavity 46 of the head unit 32. A heat sink is not required within the internal cavity 46 of the head unit 32, though. This is because the head unit 32 does not include the integrated light source 42 therein, and thus there is not a need to include a heat sink within the internal cavity 46 of the head unit 32 to absorb heat from the integrated light source 42. This also is because none of the other components of the head unit 32 necessarily generate sufficient heat during use so as to require a heat sink within the internal cavity 46.

Accordingly, in some examples the head unit 32 comprises a heat sink within the internal cavity 46 of the head unit 32. In accordance with these examples, the heat sink can absorb heat that may be generated by any components of the head unit 32 during use. The heat sink can have a variety of structures, including, for example, a heat sink/heat pipe structure. Suitable heat sinks can be custom made to fit within the head unit case 33.

Also in some examples the head unit 32 does not comprise a heat sink within the internal cavity 46 of the head unit 32. This can provide advantages, including simpler structure, lower cost, and/or and lighter weight, relative to a head unit 32 that comprises a heat sink.

Also in some examples, whether or not the head unit 32 comprises a heat sink within the internal cavity 46 of the head unit 32, the head unit case 33 itself can serve as a heat sink. For example, a head unit case 33 made from titanium can absorb heat generated by any components of the head unit 32 during use, and thus may itself serve as a heat sink.

With reference to FIG. 2, FIG. 3, and FIG. 10, in some examples the head unit 32 further comprises a window 73. In accordance with these examples, the window 73 is disposed within the second aperture 48 and configured to allow the image to pass therethrough unimpeded. The window 73 can be made of a material such as, for example, sapphire glass, plastic, and/or acrylic, among others. The window 73 also can be covered with a coating such as, for example, an anti-reflective coating, a scratch resistant coating, and/or an infrared filtering coating, among others.

In some of these examples, the second aperture 48 comprises a second aperture connector 67 as discussed above, e.g. a second aperture connector 67 comprising threads, configured for connection of medical imaging scope 50 or coupler to the head unit case 33 as discussed above. In these examples, the window 73 can allow for an image transmitted by the medical imaging scope 50 that is connected at the second aperture 48, e.g. at the second aperture 48 corresponding to a threaded hole, to pass into the head unit case 33.

With reference to FIG. 10, as noted, the head unit electrical connector 34 is configured to operatively connect with the light cable electrical connector 40 through the first aperture 47. Also, the operative connection through the first aperture 47 can be accomplished such that the first aperture 47 is effectively sealed, e.g. based on sealing contact between the light cable 39 and the head unit case 33 at the first aperture 47. In some examples, the window 73, which is disposed within the second aperture 48, also effectively seals the second aperture 48. In these examples, the head unit 32 is configured to provide power to the integrated light source 42 through the first aperture 47, and the window 73 can allow for an image transmitted by the medical imaging scope 50 that is connected at the second aperture 48 to pass into the head unit case 33, without compromising hermetic integrity and/or suitability for sterilization of the head unit case 33. In these examples, the head unit 32 can be sterilized prior to surgery, and the internal cavity 46 of the head unit case 33 can remain sterile during use of the head unit 32 in the surgery and thereafter.

The window 73 can be disposed within the second aperture 48 by a variety of approaches, such as, for example, by being positioned in the second aperture 48 and sealed therein.

In some examples the wireless medical imaging system 31 further comprises a printed circuit board 74. The printed circuit board 74 can be disposed within the internal cavity 46 of the head unit case 33. The printed circuit board 74 can support and position one or more of the image sensor 35, the wireless transceiver 36, and the central processing unit 37 that also are disposed within the internal cavity 46 of the head unit case 33. The printed circuit board 74 can be made of a material such as, for example, copper, plastic, fiberglass, and/or resin, among others. The printed circuit board 74 can be attached to the internal surface 45 of the head unit case 33 for stability and/or placement. Suitable printed circuit boards 74 can be custom made.

With reference to FIG. 10 and FIGS. 12-17, in some examples the wireless medical imaging system 31 further comprises an external battery 49 that is disposed in the external cavity 44 of the head unit case 33 and that provides power to one or more of the integrated light source 42, the image sensor 35, the wireless transceiver 36, or the central processing unit 37. The external battery 49 can comprise one or more battery cells 75. The battery cells 75 can have chemistries such as, for example, lithium ion, nickel cadmium, or lithium polymer, among others. Suitable battery cells 75 are known and commercially available, e.g. LG 18650MJ1.

In some embodiments of these examples, the external battery 49 is a removable rechargeable battery 76. In these embodiments, the wireless medical imaging system 31 can further comprise a removable housing 77 for the removable rechargeable battery 76. The removable housing 77 can be made of a material such as, for example, plastic, stainless steel, and/or titanium, among others. The removable housing 77 can comprise the removable rechargeable battery 76. Accordingly, the removable housing 77 can protect the removable rechargeable battery 76 during surgery and/or sterilization. The external cavity 44 can be configured to receive the removable rechargeable battery 76 via latching of the removable housing 77 into the external cavity 44. For example, the removable housing 77 can include a latch mechanism that allows for quick removal and replacement of the removable housing 77 and the removable rechargeable battery 76 therein from the external cavity 44 of the head unit case 33.

The removable housing 77 also can further comprise a battery management system 78. The battery management system 78 can perform one or more functions. For example, the battery management system 78 can be configured to (a) regulate power output from the removable rechargeable battery 76, (b) report charge level of the removable rechargeable battery 76, and (c) protect against faults. Alternatively and/or additionally, the battery management system 78 can be configured to store information identifying the removable rechargeable battery 76 such as number of charge cycles, a unique identifier, etc. Suitable battery management systems 78 can be custom made.

Figure 17:
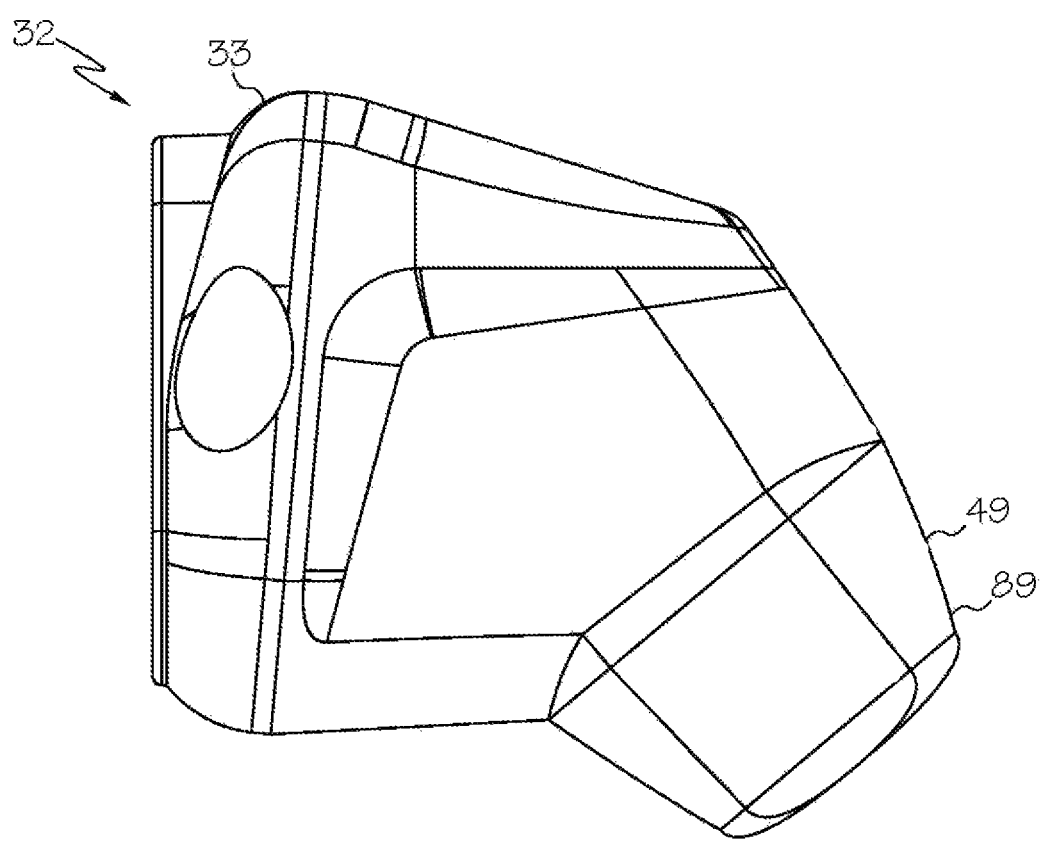
FIG. 17 shows a head unit and a non-removable rechargeable battery of an exemplary wireless medical imaging system as disclosed herein, with the non-removable rechargeable battery being attached to the head unit, in side view.
Figure 18:
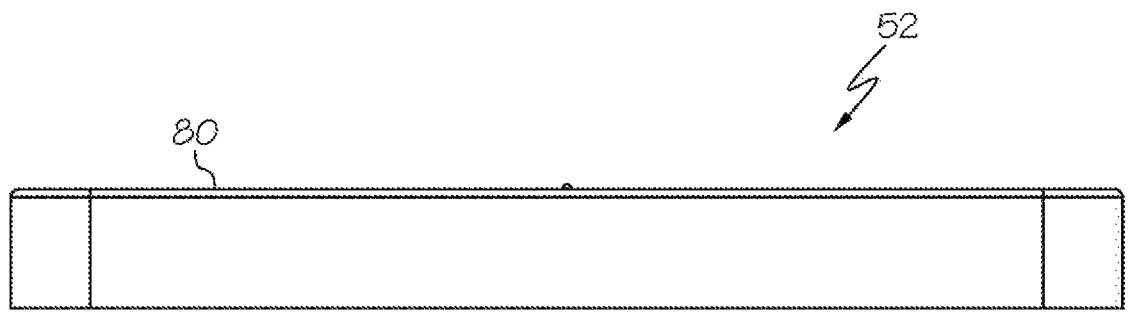
FIG. 18 shows the remote receiver unit of the exemplary wireless medical imaging system of FIG. 1, in front view.
Figure 19:
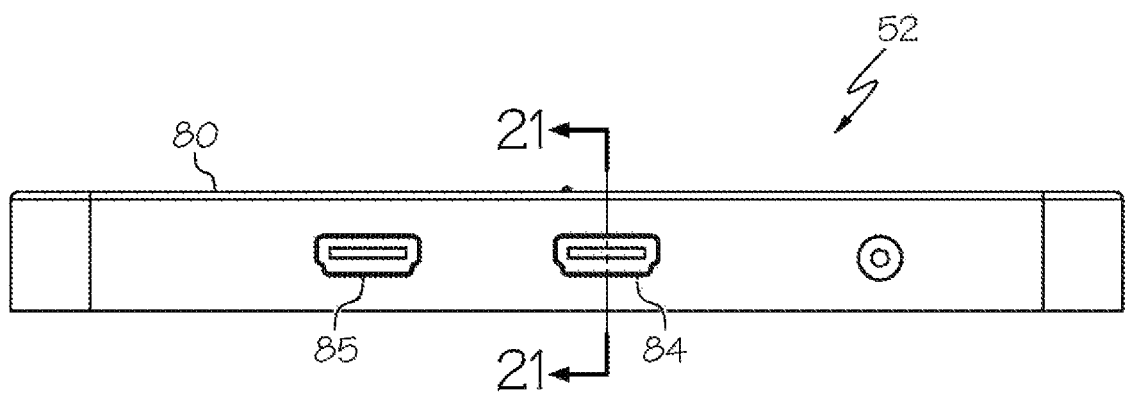
FIG. 19 shows the remote receiver unit of FIG. 18, in back view.
Figure 20:
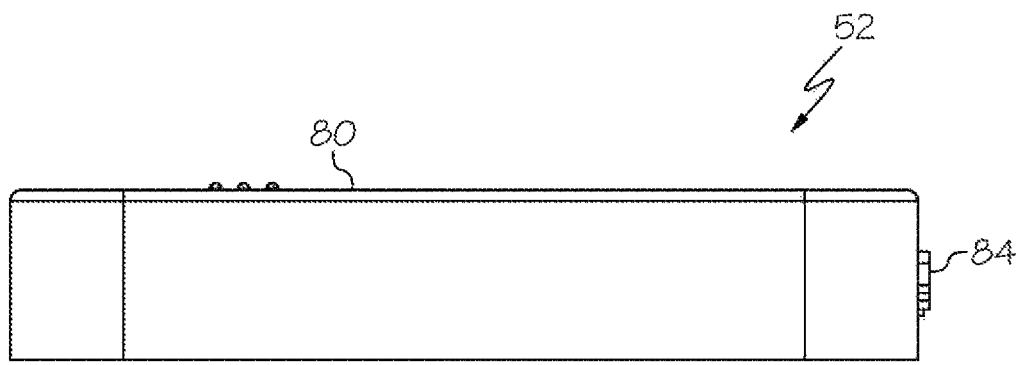
FIG. 20 shows the remote receiver unit of FIG. 18, in side view.

With reference to FIG. 17, in some embodiments of these examples, the external battery 49 is a non-removable rechargeable battery 89.

With reference to FIG. 10, in some embodiments of these examples, the external battery 49 has a high capacity and can provide adequate power to operate the integrated light source 42, the image sensor 35, the central processing unit 37, and the wireless transceiver 36. For example, the external battery 49 can have a capacity above 3,000 milliampere hours (mAh).

Also in some embodiments of these examples, the head unit 32 further comprises a power management system 79 that is configured to control power supplied by the external battery 49 and to distribute the power to the one or more of the integrated light source 42, the image sensor 35, the wireless transceiver 36, or the central processing unit 37. Suitable power management systems 79 can be made from commercially available components, including e.g. Texas Instruments TPS63020DSJ.

With reference to FIG. 1 and FIGS. 18-21, in some examples the wireless medical imaging system 31 further comprises a remote receiver unit 52. The remote receiver unit 52 comprises a receiver unit case 80, a wireless transceiver 51, a central processing unit 81, and a communications interface 82. The receiver unit case 80 has an internal cavity 83 that contains the wireless transceiver 51 of the remote receiver unit 52, the central processing unit 81 of the remote receiver unit 52, and the communications interface 82. The receiver unit case 80 can be made of a material such as, for example, plastic, stainless steel, and/or titanium, among others. Accordingly, the receiver unit case 80 can protect the wireless transceiver 51 of the remote receiver unit 52, the central processing unit 81 of the remote receiver unit 52, and the communications interface 82, as well as any other components internal to the receiver unit case 80, e.g. in the internal cavity 83 of the receiver unit case 80, during surgery and/or cleaning.

In some embodiments of these examples, the wireless transceiver 51 of the remote receiver unit 52 is configured to transmit and receive image sensor data and command and control signals, both to and from the wireless transceiver 36 of the head unit 32. For example, the remote receiver unit 52 can include a first external connection 84 that provides connections for operations such as antenna functions, data transmission, and/or power transmission, among other operations. The remote receiver unit 52 also can include a second external connection 85 that can be used to connect the remote receiver unit 52 to an endoscopy system, including, for example, any of various existing state-of-the-art endoscopy systems.

Also in some embodiments of these examples, the central processing unit 81 of the remote receiver unit 52 manages one or more of the wireless transceivers 51 of the remote receiver unit 52 or the communications interface 82, and can perform data processing as needed. For example, the remote receiver unit 52 can comprise multiple printed circuit assemblies that can be used for functions such as, for example, power control, wireless signal processing, computation, and/or video compression and decompression, among others.

Also in some embodiments of these examples, the communications interface 82 is configured to communicate with multiple types of external camera management systems without needing any changes such as reprogramming, redesign, or updates.

Suitable wireless transceivers 51 of the remote receiver unit 52 are known and commercially available, e.g. as discussed above. Suitable central processing units 81 of the remote receiver unit 52 also are known and commercially available, e.g. as discussed above. Suitable communications interfaces 82 of the remote receiver unit 52 are known and commercially available, e.g. HDMI or DVI communications interfaces.

Figure 7:
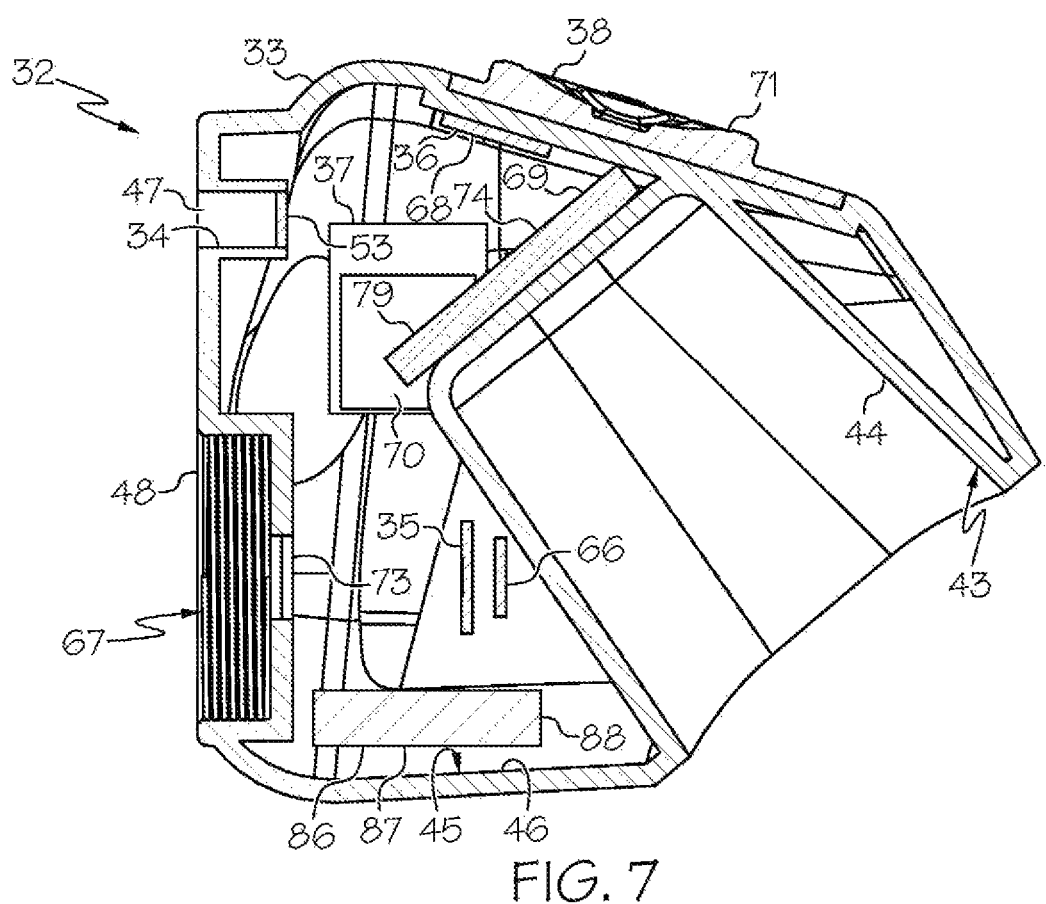
FIG. 7 shows another embodiment of the head unit of FIG. 3, wherein the head unit further comprises an internal rechargeable battery, in sectional view.
Figure 8:
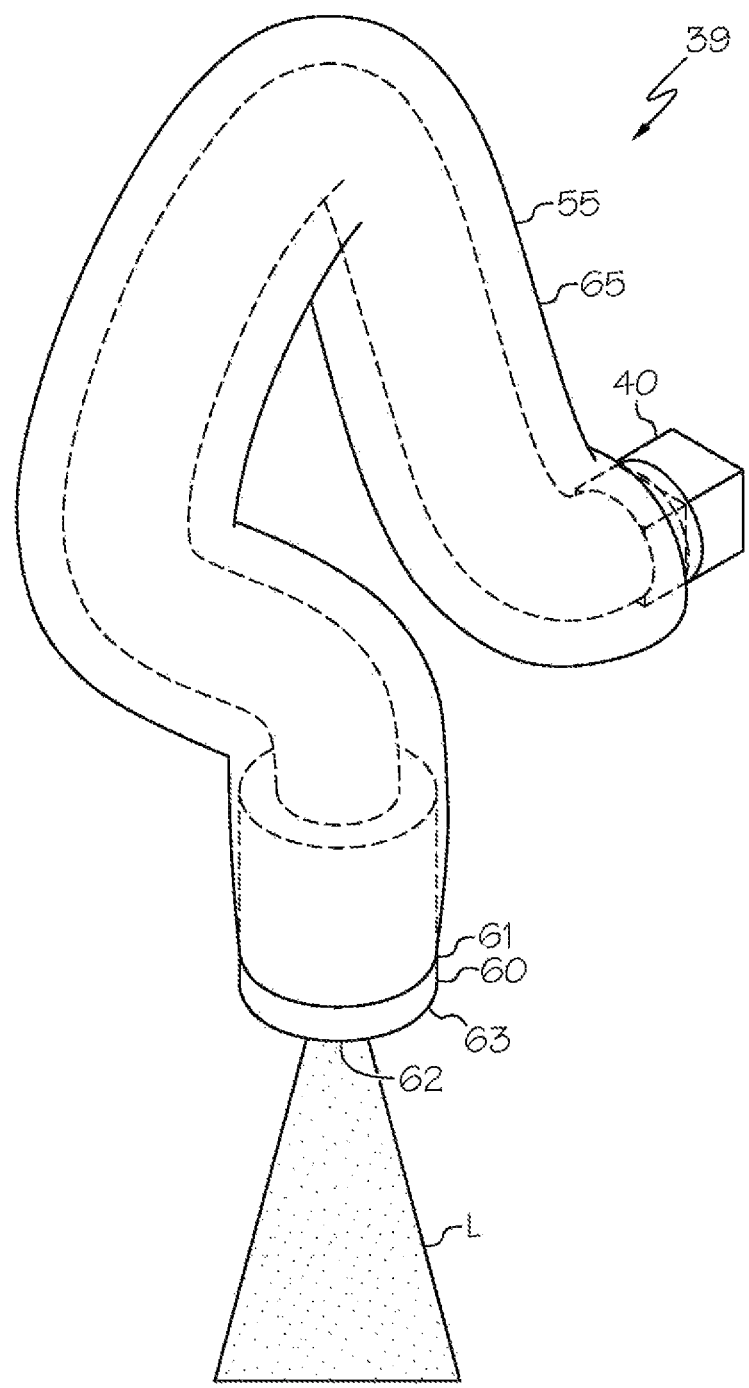
FIG. 8 shows the light cable of the exemplary wireless medical imaging system of FIG. 1, in perspective view, and transmitted light (L)

With reference to FIG. 7 and FIG. 10, in some examples the head unit 32 further comprises an internal rechargeable battery 86. The internal cavity 46 further contains the internal rechargeable battery 86.

In some embodiments of these examples, the internal rechargeable battery 86 is configured to be used as a secondary battery system 87 in case an external battery 49 ceases to provide power or is removed.

Also in some embodiments of these examples, the head unit 32 further comprises a battery management system 88 configured to manage the internal rechargeable battery 86. For example, the internal rechargeable battery 86 and the battery management system 88 of the head unit 32 allows for the integrated light source 42, the image sensor 35, the wireless transceiver 36, and the central processing unit 37 to switch to a lower power state in order to conserve power.

Also in some embodiments of these examples, the internal rechargeable battery 86 can be charged to capacity from an external battery 49.

Also in some embodiments of these examples, the internal rechargeable battery 86 is configured to be controlled by a separate power or battery management system depending on the presence of an external battery 49.

Also in some embodiments of these examples, the internal rechargeable battery 86 is sufficient to provide power for operation of the wireless medical imaging system 31.

Suitable internal rechargeable batteries are known and commercially available, e.g. as discussed above with respect to external batteries. Suitable battery management systems 88 also are known and commercially available, e.g. as discussed above.

The wireless medical imaging system 31 advantageously comprises an integrated light source 42 that provides light output that is high enough to be comparable to state-of-the-art endoscopy systems, while using less power and generating less heat than light sources conventionally used for such systems.

Considering the integrated light source 42 in more detail, with reference to FIG. 23, and as explained in more detail below, in some examples, the integrated light source 42 is an integrated light source 200 that comprises: an emissive radiation source 202 having a first spectrum; an optical element 204 located to direct emissions from the emissive radiation source 202; a volumetric spectrum converter 205, the converter 205 being located to convert emissions directed from the emissive radiation source 202 to emissions having a second spectrum different from the first spectrum; an optical reflector 206 located about the converter 205; and an output filter 207, the reflector 206 being located to reflect the converter 205 emissions towards the output filter 207. In these examples, the light cable 39 as discussed above contains the emissive radiation source 202, the optical element 204, the converter 205, the reflector 206, and the filter 207. The integrated light source 200 is configured to transmit light from the light cable 39 through the output filter 207.

In some embodiments of these examples, the emissive radiation source 202 operates in the range of 400 nm to 480 nm. The optical element 204 may either collimate, convergently focus, or divergently focus the emissive radiation source emissions onto the converter 205. The optical reflector 206 redirects omnidirectional light into a desired optical path. The converter 205 converts the emissions from the emissive radiation source 202 to emissions of different wavelength, a narrower spectrum, or a broader spectrum, of non-coherent radiation. The filter 207 eliminates an emission from the emissive radiation source 202 that has not been converted by the converter 205 as well as optionally further conditioning the emitted light. The emissive geometry of the emitted radiation spectrum from the integrated light source 200 may be further conditioned, directed, focused, collimated, reflected, refracted, diffracted, or otherwise modified with the inclusion of suitable optical components.

The light source 200 employs a solid state light emitting device pumping a medium wherein phosphor is volumetrically disposed. The light emitting device produces a beam of light that is directed onto the phosphor and subsequently converted into either a broad- or narrow-spectrum light of desired wavelengths. By using a volumetrically disposed phosphor, a higher percentage of the incoming light can be converted, thus increasing the efficiency and safety of the system. This converted light can then be sent over a desired optical path so as to control the final light output precisely.

The light source is based on a method for volumetrically disposing phosphorescent materials into a substrate. A volumetrically disposed substrate provides benefits over, for example, a current system of using a thin coating. One benefit is increased conversion of laser light into non-coherent light, which stems from the amount of phosphor available for light conversion. The current thin surface coatings of phosphor get saturated with pre-converted light quickly and can only convert a small amount of light at a time, greatly decreasing system efficiency. Attempting to increase the amount of light-converting phosphor using the current thin surface coatings of phosphor becomes extremely difficult as coherent light only travels in one direction, and thus requires the layer of phosphor to either increase in thickness, which impedes transmission and therefore effectiveness, or be distributed across a prohibitively large area. Using a volumetric deposition method allows for a larger amount of phosphor to be used in converting coherent light, without creating the need for a larger emission beam of the coherent light. An increase in the amount of phosphor being used for conversion means that more non-coherent light is produced with the same input; therefore the system is more efficient. In addition, as more coherent light is converted to non-coherent light, there is a decline in possibility that there will be dangerous coherent laser light emanating from the final light source system.

Figure 22:
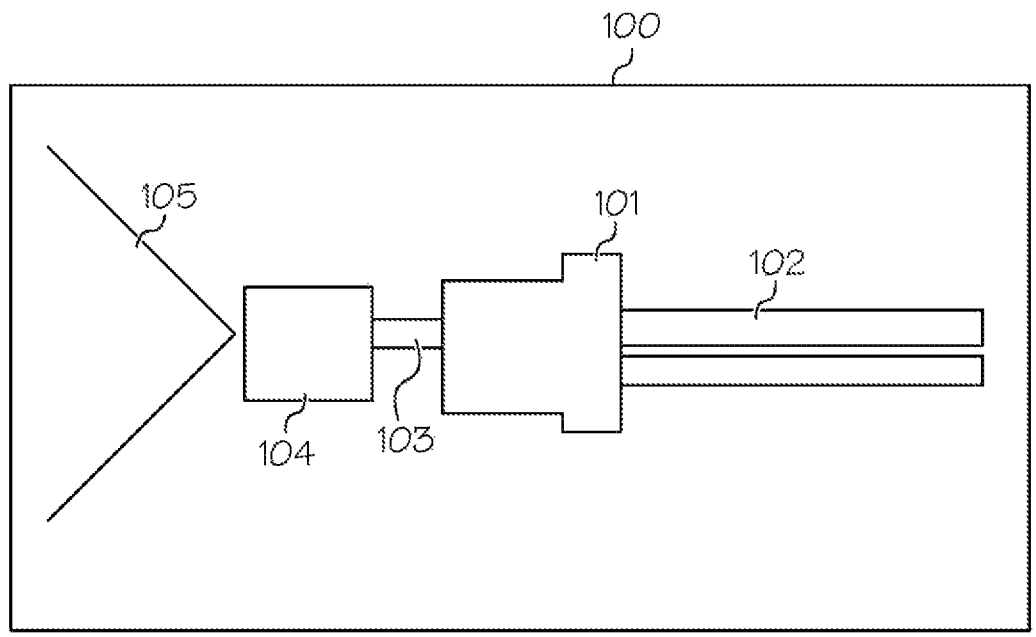
FIG. 22 is a schematic diagram of a basic solid state integrated light source as disclosed herein.

Considering light sources in more detail, referring to FIG. 22, an exemplary solid state integrated light source 100 is illustrated. The integrated light source 100 includes a laser diode 101 in the form of a semiconductor laser disposed inside of a standard electronics component package. The laser diode 101 has power pins 102 exiting the package. The laser diode 101 may, for example, provide coherent light within the range of 400-480 nm and, preferably, 430-470 nm. Beam 103 is the coherent beam of laser light that the laser diode 101 produces. Beam 103 strikes, and interacts with, volumetric spectrum converter 104 (e.g., PMMA, which is volumetrically disposed with particles of phosphor). Converter 104 thusly converts the incoming coherent laser beam 103 into outgoing broad spectrum light 105. The light 105 may be of any specified color, such as, but not limited to, white, and is decided by the chemical composition of the phosphor disposed in the medium of the converter 104.

Referring to FIG. 23, the integrated light source 200 as discussed above is illustrated. The integrated light source 200 includes an emissive radiation source 202 having a first output spectrum, for example, in the form of a semiconductor laser diode disposed inside of a standard electronics component package. The laser diode has power pins 203 exiting the package. Situated in front of the emission side of the emissive radiation source 202 is an optical element 204 composed, for example, of a lens, or system of lenses, that directs the coherent laser light emitted from the laser diode 202 onto a specific area. The optical element 204 may, for example, collimate, convergently focus, or divergently focus the emissions of the emissive radiation source 202 for conversion by the volumetric spectrum converter 205. The volumetric spectrum converter 205 converts the emissions from the emissive radiation source 202 to emissions having a second spectrum different than the first spectrum. The volumetric spectrum converter 205 is disposed inside of a geometric optical reflector 206 which is in this embodiment, but is not limited to, a parabolic solid that directs the light converted by the converter 205 towards a specified direction, which, in this case, is forward towards an output filter 207. After the light has been directed forward by the optical reflector 206, the light interacts with the filter 207 which removes any coherent light that has not been converted into non-coherent light by the converting medium of the converter 205. Following this, only the filtered, non-coherent light can exit the light source 200 making the emitted light safe to use in multiple environments. Referring to the light source 200, all aforementioned components are situated in an internal cavity 208 which is excised from a package body 201, which may be, for example, a piece of solid material such as, but not limited to, aluminum, steel, or copper.

Figure 24:
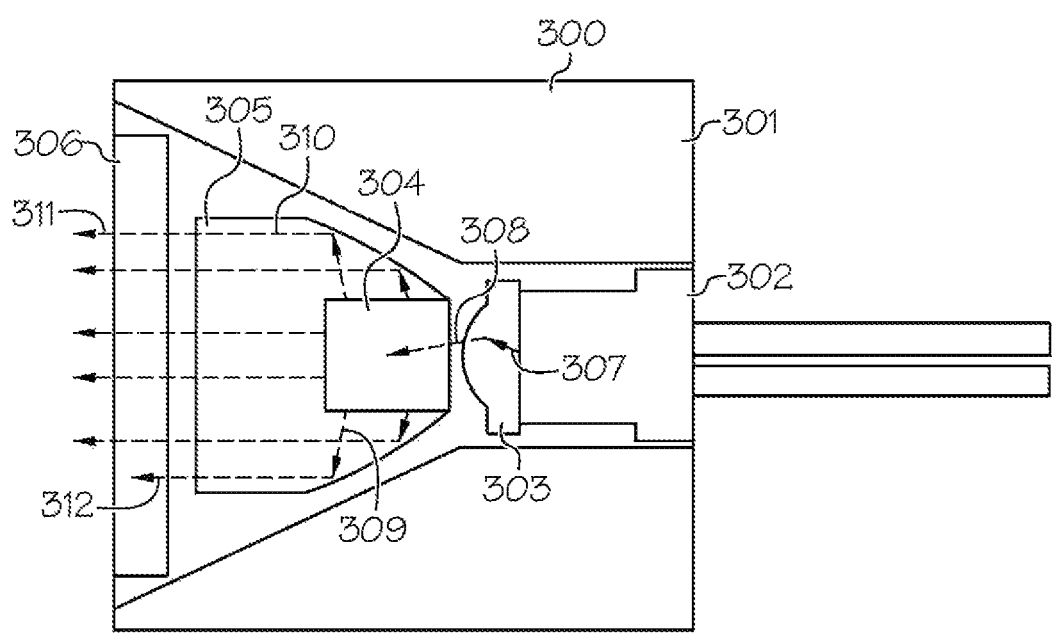
FIG. 24 is a schematic diagram that uses the integrated light source of FIG. 23 and illustrates a possible beam path for the light in the system.

Referring to FIG. 24, a possible light path using the light source seen in FIG. 23 is illustrated. The light source 300, which is comparable to the light source 200 of FIG. 23, includes a package body 301, which is comparable to package body 201 of FIG. 23. Within the light source 300 is positioned a laser diode 302 in the form of a semiconductor laser disposed inside of a standard electronics component package. The laser diode 302 emits a beam of coherent light 307, which proceeds to interact with optical element 303. The optical element 303 redirects the coherent beam 307 into a more precise path 308, which allows it to interact more efficiently with the volumetric spectrum converter 304. The converter 304 converts the coherent light 308 into non-coherent light 309 through internal physical interaction between the coherent light 308 with the volumetrically disposed phosphor present in the converter 304. Subsequently the non-coherent light 309 is emitted in multiple directions from the converter 304. The non-coherent light 309 then interacts with the geometric optical reflector 305. This optical reflector 305 reflects the non-coherent multidirectional light 309 and redirects it forward 310. Most of the redirected light 310 passes through the filter 306 and leaves 311 the light source 300. Some of the redirected light 310 interacts with the filter 306 and is prevented 312 from exiting the device for reasons such as design and safety specifications.

Figure 25:
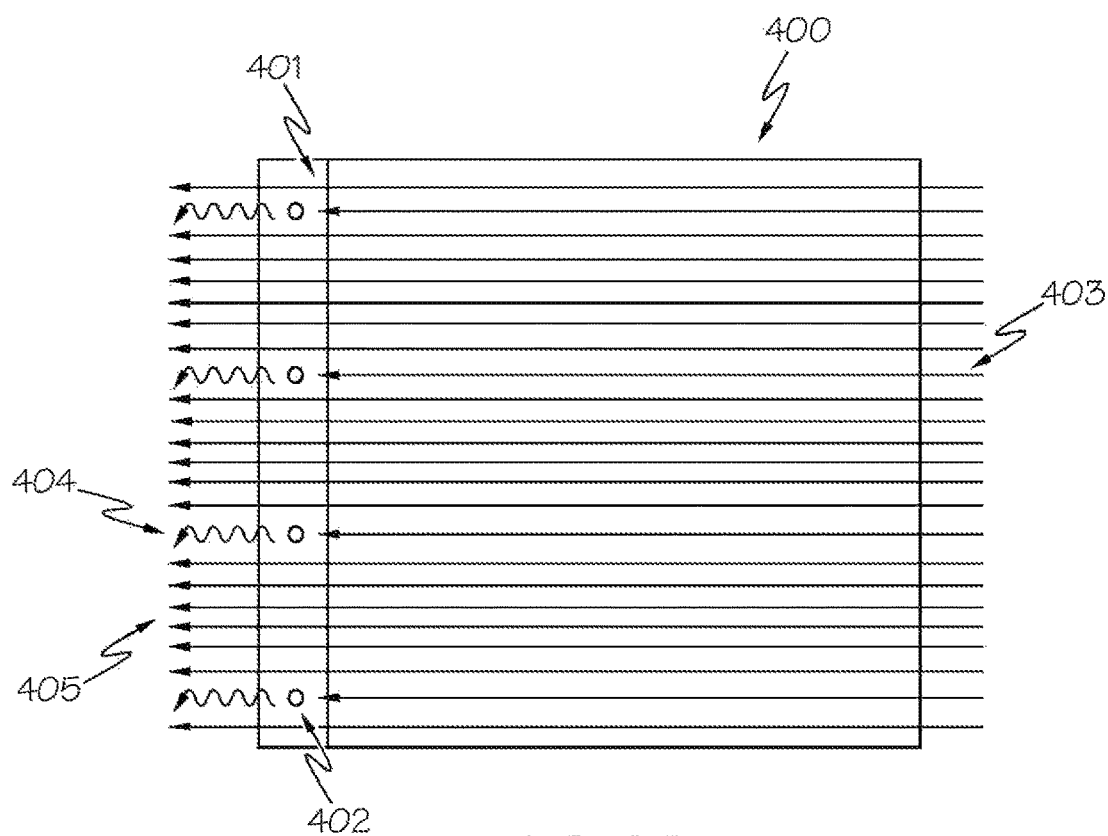
FIG. 25 is a schematic diagram of the operation of a phosphor coated converter.

FIG. 25 illustrates a phosphor coated converter. The portion 401 is a thinly deposited phosphor coating on a substrate 400. The thin phosphor coating 401 has particles of phosphor 402 that are disposed within the coating. The particles 402 convert light coming in from the right side 403 into a different wavelength of light 404. Because the coating layer 401 is thin, there is a limited amount of phosphor particles 402 that can convert the incoming light 403. Therefore, a large portion of the incoming light 403 is not converted, and leaves the substrate unaffected 405.

Figure 26:
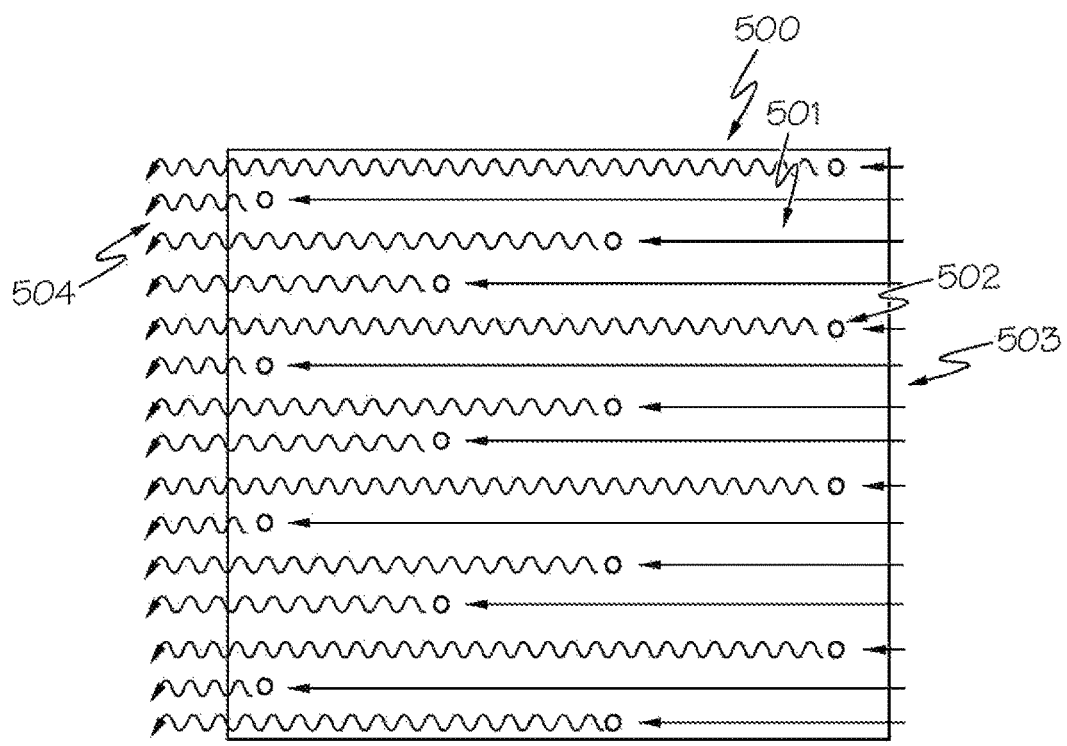
FIG. 26 is a schematic diagram of the operation of an example volumetric spectrum converter according to an aspect of the integrated light source disclosed herein.

FIG. 26 illustrates a volumetric spectrum converter, as opposed to the coating in FIG. 25. In this case, the phosphor 501 is volumetrically disposed within the substrate 500. This leads to more particles of phosphor 502 that can interact with the incoming light 503, and therefore participate in light conversion. Here there is a much larger amount of incoming light 503 that gets converted into the desired wavelength 504. The use of a volumetric spectrum converter outperforms phosphor coated converters.

It should be noted that this is a simplification for clarity. The emitted light does not necessarily come out of the front all together. It is generally scattered omnidirectionally, and the reflective paraboloid (e.g., 206, 305) of the light source is what makes the light go in the same direction.

The optical reflector may be, for example, a molded, machined, 3-D printed or otherwise fabricated piece of optical material such as PMMA, polystyrene, polycarbonate, polyester, copolymers or blends of a combination of the aforementioned materials. It is designed to redirect omnidirectional light into a desired optical path. It may be, for example, a solid geometric form, a hollow geometric form, or other combinations of geometric surfaces. It may also advantageously include a layer of reflective material that enhances its capacity to redirect light. This layer may be, for example, an external surface, an internal surface, or a combination of surfaces.

The converter (e.g., 205, 304) may be chosen to convert emissions from the emissive radiation source (e.g., blue or violet light) to radiation of another wavelength, for example, narrow or broad spectrum, non-coherent radiation. It may be made using converting material that may include, for example, phosphorescent material, florescent material, other radiation converting material, or combinations of these materials. The converting material is volumetrically disposed in a substrate that may include, for example, PMMA, polystyrene, polycarbonate, polyester, copolymers or blends of a combination of the aforementioned materials to create an effectively homogenous composite. This process may include, for example, extrusion, coating, lamination, blending, mixing, or suspending.

A particular example of making a converter is extruding a substrate with the converting material as a blended and/or multilayered solid composite. In particular, the solid composite can be made with between 2 and 500,000 layers which can be tuned for specified end use performance metrics. It is desirable for the converter to not have any defects, such as, for example, voids, entrapped gas, air bubbles, adulterating particulate of any material other the those purposely desired, or entrapped liquid of any sort, either vapor or liquid state, larger than 1 micron.

The converter can possess a ratio of converting material, or a combination of multiple materials to the substrate, that can be tuned for specified end use performance metrics.

In a preferred embodiment, the converting material may be of a single phosphor with a particular particulate size, or a mix of phosphor powders with either similar or dissimilar particulate sizes providing an emission of radiation that is either of a stable and/or variable wavelength. The emitted radiation can be for example, white light.

In another preferred embodiment, the converter possesses a ratio of converting material to the substrate between 5% and 15%.

It is also possible to tune the converter for specified end use performance metrics by varying the thickness and diameter of the converter. For example, a preferred embodiment includes a converter with a thickness of between 0.5 mm and 5 mm and a radius of between 0.5 mm and 5 mm.

The output filter (e.g., 207, 306) may be, for example, an optically clear window, but in the preferred embodiment, it eliminates any emitted radiation from the emissive radiation source that has not been converted by the converter. It also may be, for example, a long-pass, short-pass, band-pass or band-stop filter to further pass or cutoff wavelengths of radiation, to further condition the emitted light.

It should be further noted that the emissive geometry of the emitted radiation spectrum from the device may be further conditioned, directed, focused, collimated, reflected, refracted, diffracted, or otherwise modified with the inclusion of suitable optical components.

Figure 27:
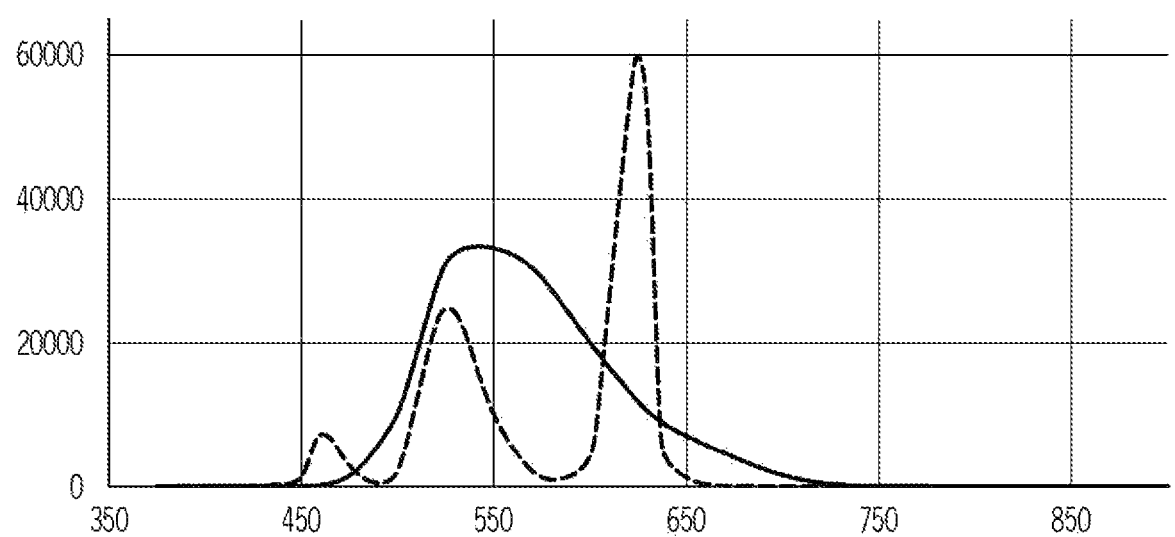
FIG. 27 is a graph comparing exemplary spectra (Y-axis: intensity; X-axis: wavelength (nm)) of a state-of-the-art 3-LED system (dashed line) and an integrated light source as disclosed herein (solid line).

Importantly, the integrated light source 42 as disclosed herein can be used to provide a continuous sun-light equivalent spectrum that is useful for both the human eye and modern camera systems, while at the same time providing a total light intensity that is equivalent to that of current systems at a lower power requirement. For example, as shown in FIG. 27, which is a graph comparing exemplary spectra of a state-of-the-art 3-LED system (dashed line) and an integrated light source as disclosed herein (solid line), current systems such as the state-of-the-art 3-LED system have three peaks corresponding to the three LED colors used. While the human eye can add these together and perceive a decent approximation of white light, modern camera systems are more sensitive and may exhibit deficiencies where there are gaps in a spectrum. By providing a continuous sun-light equivalent spectrum, the light source as disclosed herein overcomes such deficiencies, and does so while providing an equivalent total light intensity (integrals of both graphs are similar) at a lower power requirement.

The wireless medical imaging system disclosed herein provides many advantages, including the following.

The wireless medical imaging system eliminates the need for the many cables associated with conventional endoscopy systems. The wireless medical imaging system can provide a light cable including an integrated light source, a removable and hot-swappable battery system, and an FCC-compliant, FDA-approved, and HIPAA-compliant wireless modality for data transmission. The wireless medical imaging system can be integrated easily, even drop-in compatible, to current endoscopy systems, surgical workflows, and operating rooms.

The external battery, which can be in the form of a battery pack, can be made of a sufficient number of cells that, when fully charged, can last through the average length of a complete surgery, without needing to be changed. Also, if the battery pack is not fully charged before a surgery, or if a surgery takes longer than the battery charge lasts, then the battery pack can be hot-swapped with minimal disruption to the surgery performance and time.

The integrated light source can be of a range of modalities, providing light output that is bright enough to be comparable to state-of-the-art endoscopy systems, and small enough to be disposed within the light cable of the wireless medical imaging system. This eliminates the need for a long external light transfer cable extending from an endoscopy cart, and the associated need to compensate for the amount of light lost through the external light cable. This also eliminates the need for transmission of light along even a short fiber optic cable from the head unit, because the integrated light source is a component of the light cable, not the head unit, and because the light cable electrical connector, the power cable, and the integrated light source are operatively connected in series, and thus the integrated light source can be positioned at or close to an end of the light cable. This in turn allows for the light source to provide an amount of light to surgical areas that is comparable, or even greater than, the amount of light provided by state-of-the-art endoscopy systems, while using less power and emitting less waste heat. In addition, the absence of a long light transfer cable allows surgeons to have a much higher degree of flexibility in manipulating an endoscope. This eliminates the tripping hazard that an external light cable creates, and provides for much easier and more comprehensive sterilization. The use of a light cable that includes a power cable and the integrated light source, instead of a fiber optic cable, also greatly increases functionality and durability of the light cable, given that power cables generally can be made thinner and more flexible than fiber optic cables, thus providing physicians with greater ease of use with respect to manipulation of the head unit, while also reducing a risk of damage to the light cable itself, e.g. by kinking. The integrated light source also generates less heat, decreasing the possibility that materials in the operating room will catch fire from hot cables and/or other hot/radiative components.

State-of-the-art image sensors, having increased low-light sensitivity, decreased power requirements, increased resolution, and a number of improvements with regard to smart features such as automatic white balancing, automatic exposure, and automatic tone correction, can be used. This allows for a further reduction in the light output required from the integrated light source to adequately illuminate the surgical area without diminishing image quality, thus making the system more energy efficient, while still providing clear and workable images to surgeons.

The head unit can be operated without a data cable attached thereto. State-of-the-art endoscopy systems use a data cable to transfer images from a camera head unit to a camera control unit located on an endoscopy cart. While this data cable is usually thinner and more flexible than an external light cable, this data cable presents the same problems of motion restriction, tripping concerns, and sterilization difficulty. The medical imaging system described above includes a wireless transmission modality that can transfer the large amount of data needed for latency free, real-time video and command and control signals in a way that is compliant with relevant laws and regulations. While there are many wireless transmission modalities that have the capability to transfer the amount of data at the speed required, there are very few that are FDA or FCC approved for use in an operating room. Likewise, of the modalities that are approved for use in the operating room, most lack the necessary bandwidth to accomplish the transmission task, e.g. transfer of 1080p or higher video data at a minimum of 30 frames per second. For the few modalities that are both approved for use in an operating room and that have an appropriate bandwidth capacity to transfer video data within required performance parameters, it is believed that none had been used previously for duplex transmission between a surgical device to a monitor or controller, as disclosed herein.

The wireless medical imaging system can also be designed to be drop-in compatible with other endoscopy systems that are most commonly used, thus allowing easy adoption of the wireless medical imaging system in operating rooms. These improvements should result in reduced setup times for operating rooms, increased safety within operating rooms, simplified, yet more efficacious, sterilization, and improved usability and flexibility for surgeons during procedures. In combination, these advances should allow for shorter and safer surgeries, improve patient outcomes, and reduce risk and costs to hospitals and surgical centers, in a broad range of surgical and/or veterinary applications, for human and/or animal patients.

It should be evident that this disclosure is by way of example and that various changes may be made by adding, modifying or eliminating details without departing from the fair scope of the teaching contained in this disclosure. The invention is therefore not limited to particular details of this disclosure except to the extent that the following claims are necessarily so limited.

The invention claimed is:

1. A wireless medical imaging system comprising:
(a) a head unit comprising: (i) a head unit case; (ii) a head unit electrical connector; (iii) an image sensor; (iv) a wireless transceiver; (v) a central processing unit; and (vi) a user-input component; and
(b) a light cable comprising: (i) a light cable electrical connector; (ii) a power cable; and (iii) an integrated light source, wherein:
the head unit case has an external surface defining an external cavity, an internal surface defining an internal cavity, a first aperture, and a second aperture;
the head unit electrical connector is configured to operatively connect with the light cable electrical connector through the first aperture;
the light cable electrical connector, the power cable, and the integrated light source are operatively connected in series;
the integrated light source comprises: (1) an emissive radiation source having a first spectrum; (2) an optical element located to direct emissions from the emissive radiation source; (3) a volumetric spectrum converter, the converter being located to convert emissions directed from the emissive radiation source to emissions having a second spectrum different from the first spectrum; (4) an optical reflector located about the converter; and (5) an output filter, the reflector being located to reflect the converter emissions towards the output filter, and the integrated light source being configured to transmit light from the light cable through the output filter;
the image sensor, the wireless transceiver, and the central processing unit are disposed within the internal cavity;
the image sensor is configured to detect an image transmitted into the head unit through the second aperture;
the external cavity is configured to receive an external battery; and
the user-input component is disposed on the external surface.

2. The wireless medical imaging system according to claim 1, wherein:
the integrated light source comprises a solid state light source that can produce continuous spectrum light; and/or
output of the integrated light source has a spectral bandwidth that is nominally 480 nm to 775 nm.

3. The wireless medical imaging system according to claim 1, wherein the emissive radiation source operates in the range of 400 nm to 480 nm.

4. The wireless medical imaging system according to claim 1, wherein the filter eliminates an emission from the emissive radiation source that has not been converted by the converter as well as optionally further conditioning the emitted light.

5. The wireless medical imaging system according to claim 1, wherein the integrated light source is configured to provide illumination to an area of interest by connection of the light cable to a medical imaging scope, such that the light is transmitted from the integrated light source, into the medical imaging scope, to the area of interest.

6. The wireless medical imaging system according to claim 5, wherein the light cable further comprises a protective housing, the protective housing surrounds the integrated light source and has an opening, and the integrated light source is configured to transmit light from the light cable through the opening.

7. The wireless medical imaging system according to claim 1, wherein the light cable further comprises an adaptor coupling the light cable to the imaging scope, the adaptor being built into the protective housing.

8. The wireless medical imaging system according to claim 7, wherein the adaptor is further configured to allow rotation of the adaptor and the light cable with respect to the medical imaging scope while the light cable is connected to the medical imaging scope.

9. The wireless medical imaging system according to claim 1, wherein the light cable does not comprise a fiber optic cable.

10. The wireless medical imaging system according to claim 1, wherein the wireless transceiver of the head unit is configured to transmit and receive image sensor data and command and control signals, both to and from a wireless transceiver of a remote receiver unit.

11. The wireless medical imaging system according to claim 1, wherein the wireless transceiver of the head unit may use the ultra-wideband (UWB) communication modality.

12. The wireless medical imaging system according to claim 1, wherein the wireless transceiver of the head unit is configured to transmit data from the image sensor and command and control signals to an external system for management of medical imaging systems without need for reprogramming or redesign.

13. The wireless medical imaging system according to claim 1, wherein the second aperture comprises a second aperture connector configured for connection of a medical imaging scope to the head unit case.

14. The wireless medical imaging system according to claim 1, wherein the head unit does not comprise a heat sink within the internal cavity of the head unit.

15. The wireless medical imaging system according to claim 1, wherein the head unit further comprises a window, the window being disposed within the second aperture and configured to allow the image to pass therethrough.

16. The wireless medical imaging system according to claim 1, wherein the wireless medical imaging system further comprises an external battery that is disposed in the external cavity and that provides power to one or more of the integrated light source, the image sensor, the wireless transceiver, or the central processing unit.

17. The wireless medical imaging system according to claim 16, wherein the external battery is a removable rechargeable battery.

18. The wireless medical imaging system according to claim 16, wherein the external battery is a non-removable rechargeable battery.

19. The wireless medical imaging system according to claim 1, wherein the wireless medical imaging system further comprises a remote receiver unit, the remote receiver unit comprising: (i) a receiver unit case; (ii) a wireless transceiver; (iii) a central processing unit; and (iv) a communications interface; and further wherein the receiver unit case has an internal cavity that contains the wireless transceiver of the remote receiver unit, the central processing unit of the remote receiver unit, and the communications interface.

20. The wireless medical imaging system according to claim 1, wherein the head unit comprises an internal rechargeable battery and a battery management system, the internal rechargeable battery and the battery management system of the head unit allow the integrated light source, the image sensor, the wireless transceiver, and the central processing unit to switch to a lower power mode in order to conserve power.

* * * * *